(12) United States Patent  
Heruth et al.

(10) Patent No.: US 8,246,602 B2  
(45) Date of Patent: Aug. 21, 2012

(54) CATHETERS WITH TRACKING ELEMENTS AND PERMEABLE MEMBRANES

(75) Inventors: Kenneth T. Heruth, Edina, MN (US); Mark S. Lent, Brooklyn Park, MN (US); Justin A. Blanco, Philadelphia, PA (US)

(73) Assignee: Medtronic, Inc., Minneapolis, MN (US)

( * ) Notice: Subject to any disclaimer, the term of this patent is extended or adjusted under 35 U.S.C. 154(b) by 1699 days.

(21) Appl. No.: 10/873,764

(22) Filed: Jun. 22, 2004

(65) Prior Publication Data

US 2005/0137577 A1  Jun. 23, 2005

Related U.S. Application Data

(63) Continuation-in-part of application No. 10/745,965, filed on Dec. 23, 2003, and a continuation-in-part of application No. 10/745,719, filed on Dec. 23, 2003.

(60) Provisional application No. 60/436,294, filed on Dec. 23, 2002, provisional application No. 60/508,353, filed on Oct. 3, 2003.

(51) Int. Cl.  
*A61M 25/00* (2006.01)  
*A61K 9/22* (2006.01)

(52) U.S. Cl. .................. 604/523; 604/890.1; 604/891.1; 604/48

(58) Field of Classification Search .................. 604/523, 604/890.1, 891.1, 93.01, 20, 65–67, 500, 604/174, 175, 48, 264  
See application file for complete search history.

(56) References Cited

U.S. PATENT DOCUMENTS

| | | | |
|---|---|---|---|
| 3,384,089 A | 5/1968 | Shriner |
| 3,601,320 A | 8/1971 | Du Plessis |
| 3,868,565 A | 2/1975 | Kuipers |
| 4,173,228 A | 11/1979 | Van Steenwyk et al. |
| 4,317,078 A | 2/1982 | Weed et al. |
| 4,562,842 A | 1/1986 | Morfeld et al. |
| 4,642,786 A | 2/1987 | Hansen |
| 4,692,146 A | 9/1987 | Hilger |
| 4,705,503 A | 11/1987 | Dorman et al. |
| 4,767,400 A | 8/1988 | Miller et al. |
| 4,811,743 A | 3/1989 | Stevens |
| 4,815,478 A | 3/1989 | Buchbinder et al. |
| 4,821,731 A | 4/1989 | Martinelli et al. |
| 4,905,698 A | 3/1990 | Strohl, Jr. et al. |
| 5,003,989 A | 4/1991 | Taylor et al. |
| 5,024,655 A | 6/1991 | Freeman et al. |

(Continued)

FOREIGN PATENT DOCUMENTS

DE  31 15 763 A1  11/1982

(Continued)

OTHER PUBLICATIONS

Bernards, "Epidural and intrathecal drug movement," *Spinal Drug Delivery*, Yaksh, Ed., Elsevier Science, 1999;239-252, and title page, publication page, and table of contents (19 pgs. total).

(Continued)

*Primary Examiner* — Quynh-Nhu H Vu

(57) ABSTRACT

Devices, systems and methods for delivering one or more drugs to one or more internal body locations (such as the cerebrospinal fluid) are disclosed. In various aspects, the systems and methods may involve catheters having infusion sections with permeable membranes and one or more tracking elements that may be used to place the infusions sections on the catheters in selected locations such as the spinal region.

48 Claims, 12 Drawing Sheets

U.S. PATENT DOCUMENTS

| | | | |
|---|---|---|---|
| 5,195,965 | A | 3/1993 | Shantha |
| 5,207,642 | A | 5/1993 | Orkin et al. |
| 5,211,165 | A | 5/1993 | Dumoulin et al. |
| 5,395,328 | A | 3/1995 | Ockuly et al. |
| 5,397,304 | A | 3/1995 | Truckai |
| 5,415,633 | A | 5/1995 | Lazarus et al. |
| 5,423,877 | A | 6/1995 | Mackey |
| 5,425,723 | A | 6/1995 | Wang |
| 5,458,631 | A | 10/1995 | Xavier |
| 5,465,732 | A * | 11/1995 | Abele ............................ 600/585 |
| 5,474,552 | A | 12/1995 | Palti |
| 5,480,382 | A | 1/1996 | Hammerslag et al. |
| 5,558,640 | A | 9/1996 | Pfeiler et al. |
| 5,592,939 | A | 1/1997 | Martinelli |
| 5,603,703 | A | 2/1997 | Elsberry et al. |
| 5,697,377 | A | 12/1997 | Wittkampf |
| 5,702,372 | A | 12/1997 | Nelson |
| 5,713,923 | A | 2/1998 | Ward et al. |
| 5,720,720 | A | 2/1998 | Laske et al. |
| 5,752,930 | A | 5/1998 | Rise et al. |
| 5,801,188 | A | 9/1998 | Hassenbusch, III et al. |
| 5,820,589 | A | 10/1998 | Torgerson et al. |
| 5,913,820 | A | 6/1999 | Bladen et al. |
| 5,925,066 | A | 7/1999 | Kroll et al. |
| 5,975,085 | A | 11/1999 | Rise |
| 5,978,702 | A * | 11/1999 | Ward et al. ......................... 607/3 |
| 5,997,501 | A | 12/1999 | Gross et al. |
| 5,999,857 | A | 12/1999 | Weijand et al. |
| 6,030,358 | A | 2/2000 | Odland |
| 6,056,725 | A | 5/2000 | Elsberry |
| 6,059,739 | A | 5/2000 | Baumann |
| 6,061,587 | A | 5/2000 | Kucharczyk et al. |
| 6,093,180 | A | 7/2000 | Elsberry |
| 6,350,253 | B1 | 2/2002 | Deniega et al. |
| 6,371,929 | B1 | 4/2002 | Steele |
| 6,379,302 | B1 | 4/2002 | Kessman et al. |
| 6,381,485 | B1 | 4/2002 | Hunter et al. |
| 6,434,507 | B1 | 8/2002 | Clayton et al. |
| 6,471,688 | B1 | 10/2002 | Harper et al. |
| 6,474,341 | B1 | 11/2002 | Hunter et al. |
| 6,485,440 | B1 | 11/2002 | Gardeski |
| 6,500,130 | B2 | 12/2002 | Kinsella et al. |
| 6,512,957 | B1 | 1/2003 | Witte |
| 6,551,290 | B1 | 4/2003 | Elsberry et al. |
| 6,562,000 | B2 | 5/2003 | Thompson et al. |
| 6,578,017 | B1 * | 6/2003 | Ebersole et al. .................. 706/3 |
| 6,594,880 | B2 | 7/2003 | Elsberry et al. |
| 6,607,496 | B1 | 8/2003 | Poor et al. |
| 6,626,885 | B2 | 9/2003 | Massengale |
| 6,629,969 | B2 | 10/2003 | Chan et al. |
| 6,636,757 | B1 | 10/2003 | Jascob et al. |
| 6,738,661 | B1 | 5/2004 | Nyhart, Jr. |
| 6,893,429 | B2 | 5/2005 | Petersen |
| 6,902,544 | B2 | 6/2005 | Ludin et al. |
| 6,928,338 | B1 | 8/2005 | Buchser et al. |
| 6,942,639 | B2 | 9/2005 | Baugh et al. |
| 7,043,295 | B2 | 5/2006 | Starkebaum |
| 7,083,593 | B2 | 8/2006 | Stultz |
| 7,089,783 | B2 | 8/2006 | Ludin et al. |
| 2002/0042596 | A1 | 4/2002 | Hartlaub et al. |
| 2002/0111601 | A1 | 8/2002 | Thompson |
| 2002/0156462 | A1 | 10/2002 | Stultz |
| 2003/0032942 | A1 | 2/2003 | Theeuwes et al. |
| 2003/0045861 | A1* | 3/2003 | Petersen ....................... 604/537 |
| 2003/0097082 | A1 | 5/2003 | Purdy et al. |
| 2004/0093034 | A1 | 5/2004 | Girouard et al. |
| 2004/0143238 | A1 | 7/2004 | Lee |
| 2004/0193034 | A1* | 9/2004 | Wasicek et al. ............... 600/407 |
| 2004/0220518 | A1 | 11/2004 | Heruth et al. |
| 2004/0220543 | A1 | 11/2004 | Heruth et al. |
| 2004/0220544 | A1 | 11/2004 | Heruth et al. |
| 2004/0220545 | A1 | 11/2004 | Heruth et al. |
| 2004/0220546 | A1 | 11/2004 | Heruth et al. |
| 2004/0220547 | A1 | 11/2004 | Heruth et al. |
| 2004/0220548 | A1 | 11/2004 | Heruth et al. |
| 2004/0220552 | A1 | 11/2004 | Heruth et al. |
| 2005/0113745 | A1 | 5/2005 | Stultz |
| 2005/0137578 | A1 | 6/2005 | Heruth et al. |
| 2005/0137579 | A1 | 6/2005 | Heruth et al. |
| 2005/0277912 | A1 | 12/2005 | John |
| 2006/0241717 | A1* | 10/2006 | Whitehurst et al. ............ 607/45 |

FOREIGN PATENT DOCUMENTS

| | | |
|---|---|---|
| EP | 0 406 901 A1 | 1/1991 |
| EP | 0 778 036 B1 | 6/1997 |
| EP | 1 391 181 A1 | 2/2004 |
| EP | 1 421 913 A1 | 5/2004 |
| GB | 1 567 122 | 5/1980 |
| WO | WO 94/04938 A1 | 3/1994 |
| WO | WO 96/11624 A2 | 4/1996 |
| WO | WO 96/11624 A3 | 4/1996 |
| WO | WO 99/33406 A1 | 7/1999 |
| WO | WO 00/56215 A1 | 9/2000 |
| WO | WO 00/64367 A1 | 11/2000 |
| WO | WO 01/34050 A2 | 5/2001 |
| WO | WO 01/34050 A3 | 5/2001 |
| WO | WO 01/34051 A2 | 5/2001 |
| WO | WO 01/64124 A1 | 9/2001 |
| WO | WO 01/76497 A1 | 10/2001 |
| WO | WO 01/34050 A3 | 12/2001 |
| WO | WO 02/07810 A2 | 1/2002 |
| WO | WO 02/07810 A3 | 1/2002 |
| WO | WO 01/34051 A3 | 5/2002 |
| WO | WO 02/36184 A1 | 5/2002 |
| WO | WO 03/020354 A1 | 3/2003 |
| WO | WO2004/058336 A1 | 7/2004 |
| WO | WO 2005/007223 A2 | 1/2005 |
| WO | WO 2005/007223 A3 | 9/2005 |

OTHER PUBLICATIONS

Costello et al., "Density and Viscosity Sensing with Ultrasonic Flexural Plate Waves," 7th International Conference on Solid-State Sensors and Actuators, Jun. 7-10, 1993, Pacifico, Yokohama, Japan, 6 pgs.

Grouls et al., "General considerations in the formulation of drugs for spinal delivery," *Spinal Drug Delivery*, Yaksh, Ed., Elsevier Science, 1999;371-393, and title page, publication page, and table of contents (28 pgs. total).

Kandel et al., *Principles of Neural Science*, 3rd ed., 1991, Appleton & Lange, East Norwalk, Connecticut;695-800, and title page, publication page, and table of contents (110 pgs. total).

SynchroMed Infusion System product sheet, "*Optimizing Therapy Through Programmability*," Medtronic, Inc., Minneapolis, MN, 1995, 4 pgs.

Vanek et al., "Spasticity," [retrieved on Oct. 4,2005]. Retrieved from the Internet:<URL:emedicine.com/neuro/topic706.htm>; 22 pgs.

Albright et al., "Infusion of intrathecal baclofen for generalized dystonia in cerebral palsy" *J. Neurosurg.*, 1998; 88:73-76.

Albright et al., "Intrathecal baclofen for generalized dystonia" *Developmental Medicine & Child Neurology*, 2001; 43:652-657.

Bernards, "Cerebrospinal fluid and spinal cord distribution of baclofen and bupivacaine during slow intrathecal infusion in pigs" *Anesthesiology*, 2006; 105:169-178.

Dominguez et al., "Predictive value of intrathecal narcotic trials for long-term therapy with implantable drug administration systems in chronic non-cancer pain patients" *Pain Pract.*, 2002; 2(4):315-325.

Kroin, "Which drugs, what space?" *Ann. NY Acad. Sci.*, 1988; 531:40-47.

Kroin et al., "The distribution of medication along the spinal canal after chronic intrathecal administration" *Neurosurgery*, 1993; 33(2):226-230.

Richardson et al., "Intrathecal hypobaric versus hyperbaric bupivacaine with morphine for cesarean section", *Anesthesia & Analgesia*, 1998; 87(2):336-340.

Wall et al., *Textbook of Pain*, Fourth Edition, Churchill Livingstone, London, 1999; title page, copyright page, and table of contents, 5 pages.

\* cited by examiner

*Fig.* 9

CATHETERS WITH TRACKING ELEMENTS AND PERMEABLE MEMBRANES

RELATED APPLICATIONS

The present application is a continuation-in-part of U.S. patent application Ser. No. 10/745,965, filed Dec. 23, 2003, and titled PERMEABLE MEMBRANE CATHETERS, SYSTEMS, AND METHODS, and a continuation-in-part of U.S. patent application Ser. No. 10/745,719, filed Dec. 23, 2003, and titled TRIALING SYSTEM FOR EVALUATION OF THE EFFICACY OF THE TREATMENT, both of which are hereby incorporated by reference in their respective entireties, and both of which claim the benefit under 35 U.S.C. Section 119(e) of U.S. Provisional Application No. 60/436,294 titled CATHETERS AND METHODS FOR THERAPEUTIC SUBSTANCE DELIVERY, filed on Dec. 23, 2002, and U.S. Provisional Application No. 60/508,353 titled CATHETERS AND METHODS FOR THERAPEUTIC SUBSTANCE DELIVERY, filed on Oct. 3, 2003.

BACKGROUND

There are a number of conventional devices available for delivering drugs to a patient. More specifically, completely implantable drug delivery systems are available. Examples include the ISOMED and SYNCHROMED implantable pumps available from Medtronic, Inc., Minneapolis, Minn. USA.

Completely implantable drug delivery systems typically include a pump which stores and infuses the drug in a desired infusion mode and rate, and a catheter which routes the drug from the infusion pump to the desired anatomic site. Implantable pumps may be large and are typically implanted in areas of the body with available volume that is not completely filled with body organs, such as the abdomen. The target site for drug infusion may, however, be located at a distance from the pump. A thin flexible catheter is typically implanted to provide a guided pathway for drugs from the pump to the target location.

Implantable pumps are often used to treat neurological diseases; examples are chronic pain and intractable spasticity. These conditions require treatment for a long time, frequently for the lifetime of the patient. An implantable pump can deliver drugs at a desired rate without intervention for a long time, and make drug therapy much easier and more accurate. Large doses of oral drugs would be required since the blood-brain barrier prevents most of the drug from reaching the central nervous system. Some of the drug that is blocked by the blood-brain barrier will instead travel to other organs, and can cause undesirable side effects. A catheter can, however, penetrate the membranes that comprise the blood-brain barrier and infuse the drug directly to the target receptors.

The neurological drug receptors for many therapies, such as pain and spasticity, are located in the spinal cord. A catheter cannot be surgically connected to the spinal cord because it could damage other neurons and cause serious neurological problems. The brain and spinal cord are surrounded by cerebrospinal fluid (CSF). CSF provides a cushioning effect for the spinal cord, but also provides a vehicle to deliver substances such as proteins, glucose, and ions (e.g. sodium, calcium, and potassium) to the central nervous system. Neurological drug infusion systems are designed to utilize this property of CSF. The drug is infused into CSF and then distributed through the CSF to the receptors in the spinal cord. These systems typically rely on infusion at one location.

Other limitations of known implantable systems and methods of drug delivery is that the systems may be limited to a single reservoir from which only one drug solution can be delivered at any given time. The density of the drug solutions delivered by such systems cannot be changed after implantation of the devices.

SUMMARY OF THE INVENTION

The present invention provides systems and methods for delivering one or more drugs to one or more internal body locations (such as the CSF). In various aspects, the systems and methods may involve catheters having infusion sections with permeable membranes that develop significant back pressure to enhance uniform delivery of the drug over an infusion section; catheters that have two or more infusion sections spaced apart along the length of the same catheter; catheters that include two or more infusion sections serviced by independent lumens (such that, e.g., different drug solutions can be delivered to the different infusion sections); implantable drug delivery systems with pumps and multiple reservoirs from which drugs can be delivered; systems that are capable of delivering drug solutions with selected densities; etc.

The present invention may, in one aspect, preferably provide physicians with the ability to tailor the delivery of drugs within the spinal region. Tailored delivery of one or more drugs in accordance with the present invention may, e.g., increase the therapeutic efficacy of the drug infused by the system and may also reduce the amount of drug that reaches other sites in, e.g., the spine or brain (thus potentially reducing undesirable side effects).

In accordance with various exemplary aspects of the invention, the distribution profile of an intrathecally delivered drug solution may be modified by, e.g., varying the baricity (density) of the solution, changing the concentration or hydrophilicity/hydrophobicity of the drug (e.g., selecting a polymorph form of an agent, acid or base salt or neutral form an agent, etc.; selecting a different suitable agent; etc.) or solution carrying the drug, changing the location within the spinal cord where the drug is infused, changing the infusion rate of the drug, changing a pore size of a permeable membrane through which the drug is infused, or a combination thereof.

In some embodiments, the present invention may be in the form of a drug delivery catheter that includes an elongated body with a proximal end and distal end. The catheter includes a lumen extending from the proximal end of the body to an infusion section spaced from the proximal end of the body. The infusion section may preferably include two or more openings in a wall of the lumen within the infusion section and a permeable membrane covering the two or more openings in the infusion section. The two or more openings and the permeable membrane covering them may preferably create a back pressure in the lumen such that the drug exits the infusion section through all of the two or more openings in the infusion section when a drug is delivered to the infusion section through the lumen at a continuous rate of 1 milliliter per hour or less.

In connection with the catheters described herein, it may be preferred that the permeable membrane create a back pressure of 300 pascals or more in the lumen when the drug is delivered to the infusion section through the lumen at a continuous rate of 2 microliters per hour.

An alternative manner of characterizing the permeable membrane of the catheter described in the preceding paragraph may be based on molecular weight cut-off, e.g., where the permeable membrane has a molecular weight cut-off of 80 kiloDaltons or less.

In other embodiments, a drug delivery catheter in accordance with the present invention may be described as including an elongated body having a proximal end and distal end. The elongated body includes a lumen extending from the proximal end of the body to an infusion section spaced from the proximal end of the body. The catheter may include one or more openings in a wall of the lumen within the infusion section and a permeable membrane covering the one or more openings in the infusion section. The one or more openings and the permeable membrane covering them may preferably create a back pressure of 300 pascals or more in the lumen when the drug is delivered to the infusion section through the lumen at a continuous rate of 2 microliters per hour. The permeable membrane may, e.g., have a molecular weight cut-off of 80 kiloDaltons or less.

In still another embodiment, a drug delivery catheter in accordance with the present invention may include an elongated body with a proximal end and distal end. A lumen may extend from the proximal end of the body to an infusion section spaced from the proximal end of the body. One or more openings may be formed in a wall of the lumen within the infusion section and a permeable membrane may cover the one or more openings in the infusion section. The permeable membrane may have a molecular weight cut-off of 80 kiloDaltons or less.

In other embodiments, the catheters described herein may be used in drug delivery systems that include a drug delivery apparatus including a pump and a reservoir. The drug delivery apparatus may preferably be implantable within the body of the patient.

Various methods of using drug delivery catheters including permeable membranes according to the present invention may also be characterized on the basis of back pressures developed at specified flow rates and/or the molecular weight cut-off of the permeable membrane. For example, delivering the drug may create sufficient back pressure in the lumen such that the drug passes through all of the two or more openings in the infusion section when the drug is delivered to the infusion section through the lumen at a continuous rate of 1 milliliter per hour or less. In addition, the method may be characterized as creating a back pressure of 300 pascals or more in the lumen when the drug is delivered to the infusion section through the lumen at a continuous rate of 2 microliters per hour.

In another method of using a drug delivery catheter according to the present invention, delivering the drug may involve creating a back pressure of 300 pascals or more in the lumen when the drug is delivered to the infusion section through the lumen at a continuous rate of 2 microliters per hour.

In still another method of using a drug delivery catheter according to the present invention, delivering the drug through the infusion section may involve passing the drug out of the infusion section through all of one or more openings formed through a wall of the lumen within the infusion section, wherein the drug passes through a permeable membrane covering the one or more openings, and wherein the permeable membrane has a molecular weight cut-off of 80 kiloDaltons or less.

In some embodiments, the drug delivery catheters used in, e.g., systems of the present invention may include more than one infusion section. The infusions sections may be located along the same lumen or different lumens. It may be preferred that the different infusion sections be separated along the axial length of the catheter by a distance of, e.g., 20 mm or more. Further, the walls of the lumen may preferably be impermeable to liquids between the infusion sections such that drug delivery through the catheter is restricted to the infusion sections.

Spacing between adjacent infusion sections along the length of a drug delivery catheter may be characterized in a variety of manners. As noted above, the infusion sections may preferably be separated by an axial distance of 20 mm or more. In other embodiments, the infusion sections may be separated by, e.g., an axial distance of one human vertebral level or more. In still other embodiments, the infusion sections may be separated by, e.g., an axial distance of 40 mm or more. In other embodiments, the infusion sections may be separated by, e.g., an axial distance that is a whole number multiple of one human vertebral level (e.g., 40 mm).

In other embodiments, the catheters including multiple infusion sections as described herein may be used in drug delivery systems that include a drug delivery apparatus including at least one pump and at least one reservoir. The drug delivery apparatus may preferably be implantable within the body of the patient. It may be preferred that the pump be an implantable pump and the reservoir be an implantable reservoir.

The present invention may also include a method of infusing a drug to multiple internal body locations by delivering a drug from a reservoir to a first infusion section and a second infusion section of a catheter through a lumen, wherein the catheter includes an elongated body comprising a proximal end and a distal end. The first infusion section and the second infusion section are located along the elongated body, with the second infusion section being located between the proximal end of the elongated body and the first infusion section. The first infusion section and the second infusion section may be spaced apart from each other along the elongated body by an axial distance of 20 mm or more. The method may further involve passing the drug out of the lumen through the one or more openings in the first infusion section and passing the drug out of the lumen through the one or more openings in the second infusion section.

In still other embodiments, the present invention may provide a drug delivery catheter having an elongated body with a proximal end and a distal end. A first lumen may extend from the proximal end of the body to a first infusion section located along the elongated body which may include one or more openings in the first lumen. The catheter may also include a second lumen extending from the proximal end of the body to a second infusion section that is located along the elongated body and that is spaced apart from the first infusion section along the body by an axial distance of 20 mm or more. The second infusion section may preferably be located along the elongated body between the proximal end of the elongated body and the first infusion section. The second infusion section may also include one or more openings in the second lumen within the second infusion section.

Spacing between adjacent infusion sections along the length of a drug delivery catheter including two or more lumens may be characterized in a variety of manners. As noted above, the infusion sections may preferably be separated by an axial distance of 20 mm or more. In other embodiments, the infusion sections may be separated by, e.g., an axial distance of one human vertebral level or more. In still other embodiments, the infusion sections may be separated by, e.g., an axial distance of 40 mm or more. In other embodiments, the infusion sections may be separated by, e.g., an axial distance that is a whole number multiple of one human vertebral level (e.g., 40 mm).

In other embodiments, the catheters including multiple lumens, each with at least one infusion section as described herein may be used in drug delivery systems that include a drug delivery apparatus including at least one pump and at least one reservoir. The drug delivery apparatus may preferably be implantable within the body of the patient. It may be preferred that the pump be an implantable pump and the reservoir be an implantable reservoir.

The present invention may also preferably provide methods of delivering one or more drugs to two or more locations within the spinal region of a patient. Such a method may include delivering a first drug to a first location within the spinal region of a patient; and delivering a second drug to a second location within the spinal region of a patient; wherein the first drug and the second drug are the same or different. Delivery of the first and second drugs to the first and second locations may be performed simultaneously or not. Also, the first drug and the second drug may be delivered through the same catheter or different catheters. In some instances, the first drug may be delivered through a first lumen in a catheter and the second drug may be delivered through a second lumen in the same catheter. The catheters used in such a method may include, e.g., any suitable catheters among those described herein or other catheters that are not described herein.

The present invention may also include an implantable drug delivery system that includes an implantable pump assembly and two or more implantable reservoirs operably connected to the implantable pump assembly. The system also preferably includes a catheter connection port adapted to attach a catheter to the drug delivery system and a reservoir switching valve assembly between the two or more implantable reservoirs and the catheter connection port, wherein the two or more implantable reservoirs can be selectively connected to the catheter connection port. In some embodiments, the reservoir switching valve assembly may be optional and in such embodiments, it may be desirable to include a pump assembly that includes, e.g., two or more pump mechanisms.

Such implantable systems may include, e.g., in various embodiments: a telemetry module operably connected to control the reservoir switching valve assembly; an implantable density sensor; a telemetry module operably connected to the density sensor; means for mixing fluids delivered from at least two of the two or more reservoirs such that a mixed fluid having a selected density can be obtained based on, e.g., a density measured by the density sensor.

In such a system with multiple implanted reservoirs, two reservoirs of the two or more reservoirs contain different drugs that may, e.g., be in drug solutions having different densities. In another alternative, two reservoirs of the two or more reservoirs may contain the same drug in two different drug solutions having different densities.

Such a system may also incorporate means for modifying the flow rate to the catheter connection port such as by using an implantable pump assembly that includes at least one programmable pump mechanism, a flow restrictor, metering valve, etc.

In a system with multiple implanted reservoirs, it may be preferred to use a catheter that includes, e.g., a first lumen extending from the proximal end of the catheter to a first infusion section and a second lumen extending from the proximal end of the catheter to a second infusion section. Such a system may also preferably include a lumen switching valve assembly between the two or more reservoirs and the catheter, wherein the two or more reservoirs can be selectively connected to one or both of the first lumen and the second lumen.

In some embodiments, the system may include dedicated relationships between reservoirs and catheter lumens. For example, the two or more reservoirs may include a first reservoir connected to the first lumen of the catheter and a second reservoir connected to the second lumen of the catheter. Valves may be used to control flow through each of the lumens.

The present invention may also involve methods of delivering one or more drugs to at least one internal body location using a drug delivery system implanted in the body of a patient, wherein the drug delivery apparatus includes an implantable pump assembly, two or more implantable reservoirs operably connected to the implantable pump assembly, a catheter connection port adapted to attach a catheter to the drug delivery system, and a reservoir switching valve assembly between the two or more implantable reservoirs and the catheter connection port. The method may include, e.g., selectively connecting at least one reservoir of the two or more implantable reservoirs to the catheter connection port; and delivering a drug from at least one reservoir of the two or more implantable reservoirs to the catheter connection port using the implantable pump assembly.

In such a method, the reservoir switching valve assembly may be controlled from a location outside of the body of the patient. The method may involve, e.g., measuring density of the cerebrospinal fluid of a patient using an implanted density sensor.

In other variations, the methods may include mixing fluids delivered from at least two of the two or more reservoirs before delivering the drug. In some instances, the two reservoirs of the two or more reservoirs contain different drugs in solutions having the same or different densities. In still other instances, two reservoirs may contain the same drug in two different drug solutions having different densities.

In still other potential aspects of the present invention, the catheters and/or drug delivery systems may be used in methods of adjusting the density of a drug solution to be delivered to an internal body location of a patient. Such methods may involve, e.g., determining a selected density for the drug solution; formulating the drug solution from two or more components to obtain the selected density for the drug solution, and infusing the drug solution to an internal body location at a continuous rate of no more than 50 milliliters (ml) per hour for a period of five minutes or more. In variations on this method, the maximum infusion rate may be, e.g., no more than 25 ml per hour, no more than 10 ml per hour, no more than 5 ml per hour, or even potentially no more than 2 ml per hour. Variations may also be found in the time period over which the infusion is performed. The period of infusion may alternatively be, e.g., 10 minutes or more, one hour or more, eight hours or more, or even 24 hours or more.

In still other variations on the methods described in the previous paragraph, the infusing may preferably be performed for a period of at least 8 hours within a twenty four hour period. Alternatives to this may include, e.g., at least 12 hours within a twenty four hour period, or even at least 16 hours in a twenty four hour period.

In another manner of characterizing the invention, the infusion process may be described in terms of a duty cycle, e.g., where the infusion is performed for a duty cycle of at least 25% within a given time period, or at least 50% within a given time, or even at least 75% within a given time period. The time periods over which the duty cycle is determined may be, e.g., 8 hours or more, 12 hours or more, 16 hours or more, or even 24 hours or more.

In some methods, determining the selected density involves determining the density of the cerebrospinal fluid of a patient either in vivo (using a density sensor located within the cerebrospinal fluid of a patient) or measuring the density of the cerebrospinal fluid after removing the cerebrospinal fluid from the patient.

Formulating the drug solution may be performed outside of the body of the patient or within the body of the patient (using, e.g., some of the systems described herein). If the drug solution is formulated within the body of the patient, it may be desirable to obtain the components for the drug solution from two or more reservoirs implanted within the patient.

Because density variations can have an effect on the efficacy of a treatment plan, it may be desirable to obtain feedback regarding efficacy of the drug solution after delivering the drug solution to the patient. The method may then involve adjusting the density of the drug solution based on the feedback. The feedback may be provided by, e.g., the patient, doctors, nurses, other caregivers, sensors, etc.

In another method of adjusting the density of a drug solution, the present invention may involve determining a selected density for the drug solution; and controlling the temperature of the drug solution to increase or decrease the density of the drug solution to reach the selected density. As discussed above, determining the selected density may involve determining the density of the cerebrospinal fluid of a patient either in vivo (using a density sensor located within the cerebrospinal fluid of a patient) or measuring the density of the cerebrospinal fluid after removing the cerebrospinal fluid from the patient.

To take advantage of the use of drug solution density, it may be advantageous to employ a drug delivery system that includes a drug delivery apparatus with a pump assembly and two or more reservoirs operably connected to the pump assembly. The system may further include a catheter connection port adapted to attach a catheter to the drug delivery system and means for mixing fluids from at least two reservoirs of the two or more reservoirs at or before delivering the fluids to the catheter connection port.

Such a system designed to deliver drug solutions with selected densities may include, e.g., an implantable density sensor operably connected to the drug delivery apparatus.

In a system designed to supply drug solutions with selected densities, two reservoirs of the two or more reservoirs may preferably contain different fluids. The different fluids may, e.g., have different densities.

In one embodiment, a first reservoir of the two or more reservoirs may contain a first fluid with a low density, a second reservoir of the two or more reservoirs may contain a second fluid with an intermediate density, and a third reservoir may contain a third fluid with a high density (where the low, intermediate and high densities are relative to each other only). The second fluid may include the drug to be delivered such that addition of the first fluid lowers the density of the drug solution or addition of the third fluid increases the density of the drug solution. In some systems, the first fluid and the third fluid may be substantially free of the drug.

In another variation, at least two fluids of the first fluid, the second fluid, and the third fluid may include the same drug. In still another variation, two reservoirs of the two or more reservoirs may contain the same drug in two different drug solutions having different densities.

Density control systems may also include a thermal control device for controlling the temperature of the drug (in addition to controlling density through selective mixing of fluids having different densities).

It may be preferred that the pump assembly be an implantable pump assembly, and that the two or more reservoirs be implantable reservoirs operably connected to the implantable pump assembly, and further wherein the means for mixing is implantable means for mixing.

In another aspect, the present invention may provide a drug delivery system that includes a drug delivery apparatus having a pump assembly, one or more reservoirs operably connected to the pump assembly, and a catheter connection port adapted to attach a catheter to the drug delivery system. The system also includes a thermal control device for controlling the temperature of the drug delivered to the patient.

The thermal control device may, e.g., control the temperature of the drug before the drug is delivered to the catheter connection port. Alternatively, the thermal control device may control the temperature of the drug after the drug passes through the catheter connection port. The thermal control device may be located within a catheter connected to the catheter connection port. Such a system may also include an implantable density sensor operably connected to the drug delivery apparatus. The density sensor may be operably connected to the drug delivery apparatus, whereby a fluid having a selected temperature can be obtained based on a density measured by the density sensor. Such a system may preferably be implantable.

In various embodiments, the invention provides methods for treating a disease. The catheters and systems described herein may be employed in the methods in various embodiments. In an embodiment, the method for treating a disease comprises administering a first drug to a first spinal location and administering a second drug to a second spinal location. The first and second drugs may be the same or different. In an embodiment, the first and second spinal locations are at least one vertebral level apart. In an embodiment, the method is method for treating pain. Any pharmacologically acceptable pain drug may be administered according to the method. In an embodiment, the invention provides a method for treating spasticity. Any pharmacologically acceptable pain drug may be administered according to the method.

In various embodiments, the invention provides methods and systems for screening patients as candidates for therapy and/or for optimizing parameters associated with therapy. In various embodiments, the methods comprise administering a therapeutic composition comprising a drug to a subject, varying parameters associated with the administration of the drug, and determining the effect of varying the parameter. Parameters that may be varied include baricity of the therapeutic composition, hydrophobicity of the therapeutic composition, the drug, flow rate, location, presence of a permeable membrane and combinations thereof.

In an embodiment, the invention provides a method for reducing the formation of an inflammatory mass. The method comprises reducing the local concentration of a drug over time at a given vertebral level in a patient's spinal column. The local concentration of the drug over time may be reduced by, for example, replacing continuous infusion with intermittent bolus infusion; altering the density of a solution comprising the drug; replacing the drug with another drug; changing the concentration of the drug in a solution; and changing the vertebral location where the first drug is delivered. The various means for reducing local concentration of the drug may be employed periodically (e.g., switch between intermittent bolus infusion and continuous bolus infusion).

In an embodiment, the invention also provides a method of delivering a drug to a subject's brain via the subject's spinal column. The method comprises administering a hypobaric solution comprising the drug to the subject's cerebrospinal fluid (CSF) in the subject's spinal column. Buoyant forces will cause the drug to rise through the CSF into the subject's brain. The drug may be administered a spinal location near the brain to facilitate the entry of the drug to the brain. The drug may be hydrophilic to prolong the time the drug stays in the CSF, increasing the amount of the drug that may reach the brain. In a related embodiment, the invention provides a method of delivering a hyberbaric solution comprising a drug to a subject to reduce the amount of the drug that reaches the subject's brain.

In one exemplary embodiment, the present invention provides a drug delivery catheter that includes an elongated body with a proximal end and distal end; a lumen extending along the elongated body to a first infusion section spaced from the proximal end of the elongated body; one or more openings in the lumen within the first infusion section; a permeable membrane covering the one or more openings in the first infusion section; and a first tracking element attached to the elongated body at a first selected location relative to the first infusion section.

In another exemplary embodiment, the present invention provides a drug delivery system that includes a drug delivery apparatus with a pump and a drug reservoir. The system also includes a catheter with an elongated body having a proximal end and distal end; a lumen extending along the elongated body to a first infusion section spaced from the proximal end of the elongated body; one or more openings in the lumen within the first infusion section; a permeable membrane covering the one or more openings in the first infusion section; and a first tracking element attached to the elongated body at a first selected location relative to the first infusion section. The system also includes a tracking system adapted to determine the location of the first tracking element.

In another exemplary embodiment, the present invention provides a method of locating a drug delivery catheter within a spinal region. The method includes providing a catheter having an elongated body with a proximal end and distal end; a lumen extending along the elongated body to a first infusion section spaced from the proximal end of the elongated body; one or more openings in the lumen within the first infusion section; a permeable membrane covering the one or more openings in the first infusion section; and a first tracking element attached to the elongated body at a first selected location relative to the first infusion section. The method further includes introducing the catheter into the spinal region of a subject; tracking the tracking element on the catheter to determine the position of the first infusion section within the spinal region; and advancing the catheter into the spinal region until the first infusion section is at a selected location within the spinal region.

These and other features and advantages of the systems and methods of the present invention may be described below in connection with some illustrative examples of the present invention.

DETAILED DESCRIPTION OF ILLUSTRATIVE EMBODIMENTS OF THE INVENTION

Figure 1A:
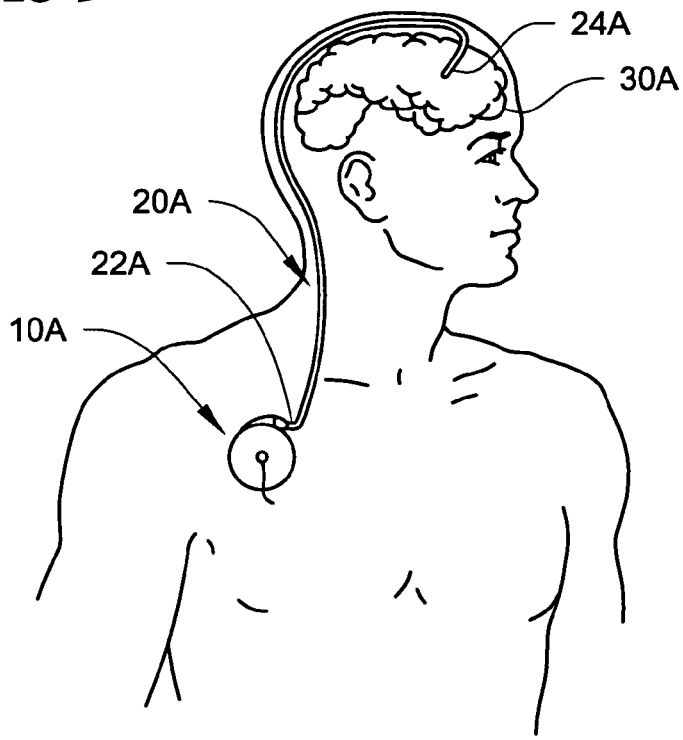
FIG. 1A is a schematic diagram of one drug delivery system implanted within the body of a patient and infusing drug into the brain.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention may be used in connection with a variety of methods, catheters and/or systems as may be described in, e.g., U.S. patent application Ser. No. 10/745,965, filed Dec. 23, 2003, titled PERMEABLE MEMBRANE CATHETERS, SYSTEMS AND METHODS; U.S. patent application Ser. No. 10/745,919, filed Dec. 23, 2003, titled MULTIPLE INFUSION SECTION CATHETERS, SYSTEMS AND METHODS; U.S. patent application Ser. No. 10/746,269, filed Dec. 23, 2003, titled IMPLANTABLE DRUG DELIVERY SYSTEMS AND METHODS; U.S. patent application Ser. No. 10/745,963, filed Dec. 23, 2003, titled DRUG SOLUTION DENSITY ADJUSTMENT SYSTEMS AND METHODS; U.S. patent application Ser. No. 10/745,897, filed Dec. 23, 2003, titled REDUCTION OF INFLAMMATORY MASS WITH SPINAL CATHETERS; U.S. patent application Ser. No. 10/745,750, filed Dec. 23, 2003, titled METHOD FOR DELIVERING DRUGS TO SPECIFIC REGIONS OF THE SPINAL CORD; U.S. patent application Ser. No. 10/745,719, filed Dec. 23, 2003, titled TRIALING SYSTEM FOR EVALUATION OF THE EFFICACY OF THE TREATMENT; and U.S. patent application Ser. No. 10/745,731, filed Dec. 23, 2003, titled METHOD FOR DELIVERING DRUG TO BRAIN VIA SPINAL CORD.

The present invention relates to the delivery of drugs. For the purposes of the present invention, the term "drug" means any pharmacological or therapeutic agent or combination of agents delivered to provide therapy to a patient (human or non-human animals). The drugs will typically be liquids or materials contained in liquid carriers as either solutions or mixtures (although where used herein, the term "solution" refers to both solutions and mixtures).

Furthermore, although in many instances, the catheters, drug delivery systems, methods and other aspects of the invention may be useful in connection with delivery of one or more drugs to the spinal region, it should be understood that the present invention may find use in connection with delivery of one or more drugs to other internal body locations as well, including, but not limited to, the brain or any other suitable anatomical location.

As used herein, the term "spinal region" includes the spinal canal (including the spinal cord, intrathecal space, dura, epidural space, etc.), vertebra, spinal discs, nerve roots, and the ligaments, tendons and muscles in between and surrounding the vertebra.

Figure 1B:
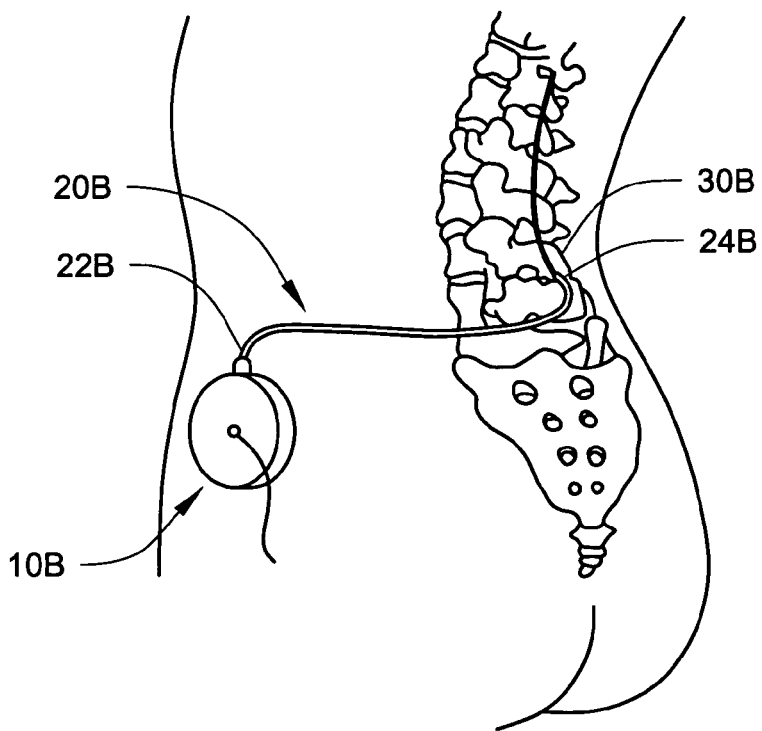
FIG. 1B is a schematic diagram of one implanted drug delivery system for infusing drug directly to the spinal region.
Figure 1C:
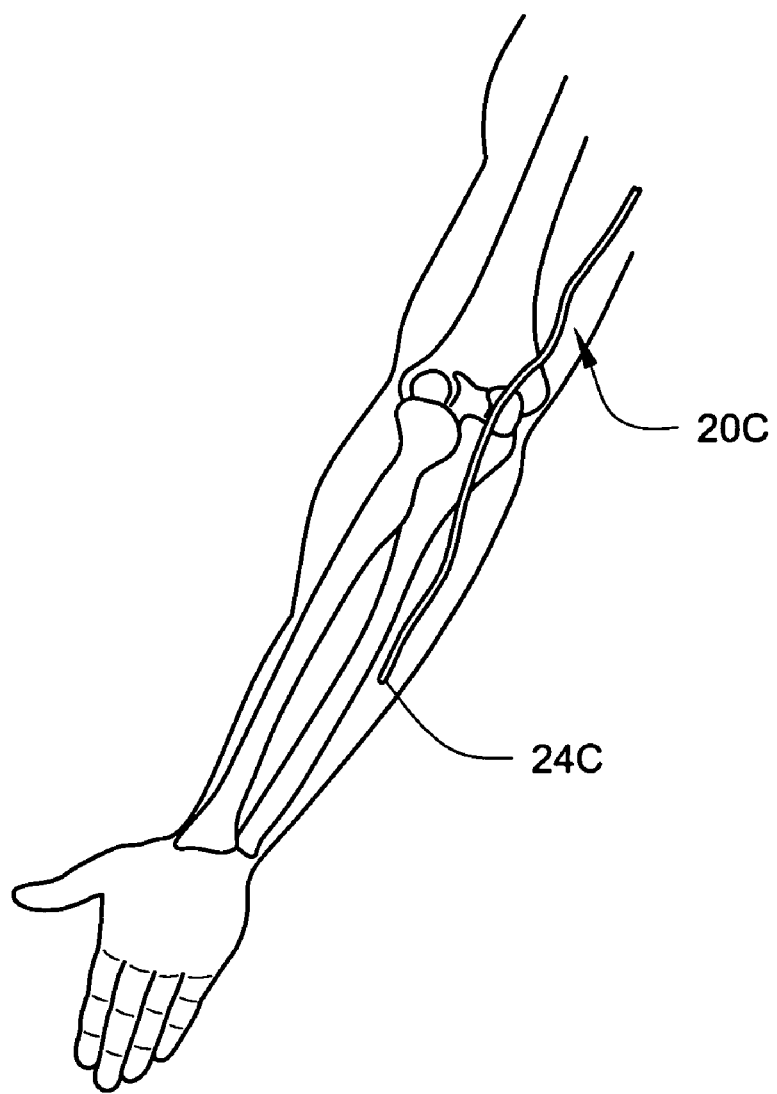
FIG. 1C is a schematic diagram of one implanted drug delivery system for infusing drug directly to the peripheral nervous system.

Exemplary embodiments of some drug delivery systems for infusing drugs are depicted in FIGS. 1A, 1B, and 1C. FIG. 1A is a schematic diagram of a drug delivery system for infusing drug to the brain, FIG. 1B is a schematic diagram of a drug delivery system for infusing drug to the spinal region, and FIG. 1C is a schematic depiction of a drug delivery system for infusing drug to the peripheral nervous system.

The drug delivery systems depicted in FIGS. 1A and 1B includes a drug infusion pump assembly 10A/10B and catheter 20A/20B having a proximal end 22A/22B attached to the pump assembly and distal end 24A/24B implanted within the patient. The distal end 24A is implanted within the brain of the patient, while the distal end 24B is implanted within the spinal column 30 of the patient.

FIG. 1C depicts only a portion of the drug delivery system, namely the portion of catheter 20C including its distal end 24B, which is implanted to infuse drugs to the peripheral nervous system. The depicted infusion site in the arm is provided as exemplary only, with the systems of the present invention capable of infusing drugs to any internal body location.

Furthermore, although the systems of FIGS. 1A, 1B, and 1C are depicted infusing drugs into only one area, e.g., brain, spinal region or peripheral nervous system, it should be understood that a single system could infuse one or more drugs to one or more locations in any one or more of the brain, spinal region and/or peripheral nervous system. Also, although depicted in connection with a human body, it should be understood that the drug delivery systems of the present invention could also be used on non-human animals.

The pump assembly 10 may preferably be surgically implanted subcutaneously in the pectoral or abdominal region of the subject's body. The pump assembly 10 may be any suitable mechanism capable of delivering one or more drugs to a patient. The pump assembly 10 preferably includes a pumping mechanism, at least one reservoir containing the drug to be delivered, and a power supply to operate the pump assembly 10 such that the drug is delivered to the patient at a selected rate. Examples of some suitable pumps may include, e.g., commercially available implantable infusion pumps such as, for example, the SYNCHROMED pumps, Models 8611H, EL 8626, and EL 8627, manufactured by Medtronic, Inc., Minneapolis, Minn. It should be understood that some pumps used in connection with the present invention may not require a separate power supply.

While an implantable pump assembly 10 is depicted, it should be understood to those skilled in the art that the device used to deliver drug to the catheter may be either implanted or extracorporeal. As used herein, the term "implantable" means that the system, apparatus or device is adapted for implantation in the body of subject where it is located at least subcutaneously.

Figure 2:
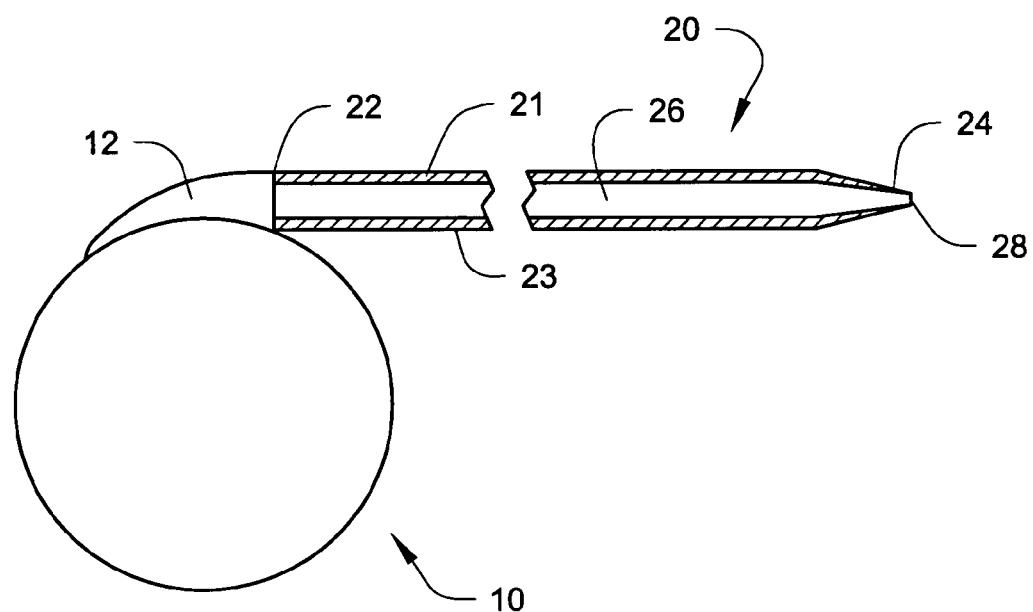
FIG. 2 depicts an enlarged view of a drug delivery system similar to that depicted in, e.g., FIG. 1B.

One exemplary structure of a pump assembly 10 and catheter 20 may be understood by reference to FIG. 2, which depicts one embodiment of the system with a portion of the catheter 20 shown in an enlarged half section. The size of the catheter 20 is exaggerated for ease of illustration of the structure thereof and the full length of the catheter 20 is not shown for simplicity of illustration. The proximal end 22 of the catheter 20 is coupled to the pump connector 12. The connection between the catheter 20 and the pump connector 12 is shown schematically in FIG. 2. It should be understood that the actual type of connection between the pump connector 12 and the catheter 20 will vary depending upon the particular type of pump assembly 10 utilized.

The catheter 20 includes an elongated tubular portion 23 that preferably extends from the proximal end 22 to the distal end 24. The catheter 20 depicted in FIG. 2 includes a lumen 26 that terminates at opening 28 at the distal end 24. Drug delivered from the pump assembly 10 to the catheter 20 passes through lumen 26 and exits the catheter through opening 28.

When implanted for delivering drugs to, e.g., the spinal region, it may be preferred that at least a portion of the catheter 20 be located within the CSF of the patient such that as drug exits the catheter 20 it enters directly into the CSF. By "directly," it is meant that the drug preferably does not contact other tissues or bodily fluids before reaching the CSF of the patient.

The body of catheter 20 may preferably be constructed of any suitable material, e.g., an elastomeric tube. If used in the spinal canal, the catheter 20 may be floating free in the CSF and may contact the spinal cord. As a result, in such an application the catheter 20 may preferably be soft and flexible to limit any chance of damaging the spinal cord. Examples of some suitable materials include, but are not limited to, silicone rubber (e.g., polydimethyl siloxane) or polyurethane, both of which can provide good mechanical properties and are very flexible. Suitable materials for the catheter 20 are also preferably chemically inert such that they will not interact with drugs or body tissue or body fluids over a long time period.

Figure 3:
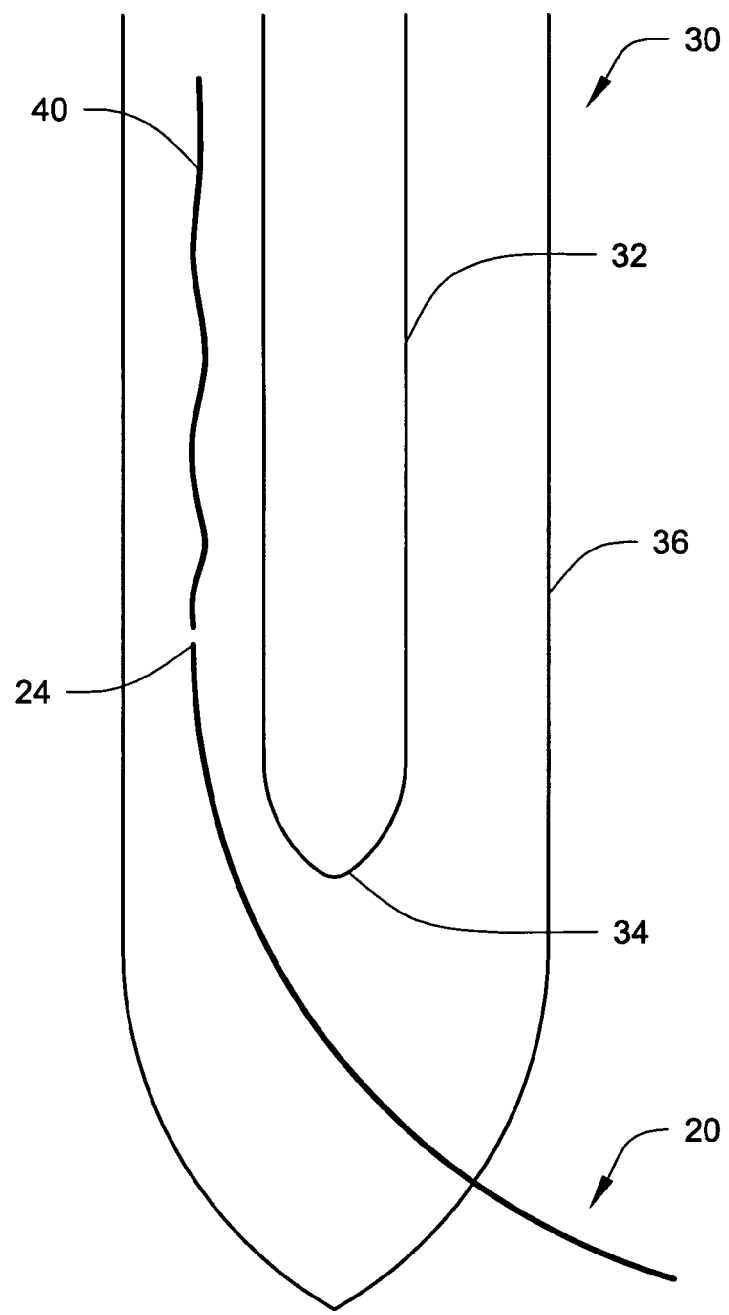
FIG. 3 depicts the distal end of the catheter of FIG. 2 infusing drug into the spinal region.

In some embodiments, the catheter may preferably be sized to fit in the gap between the spinal cord 32 and the dura 36 (see, e.g., FIG. 3). The inside diameter, e.g., the diameter of the lumen 26, is preferably large enough to accommodate expected infusion rates with acceptable flow resistance. The wall 21 of the catheter 20 is preferably thick enough to withstand normal handling during the implant procedure and forces from body tissues during normal motion. As an example, the catheter 20 may have an outside diameter of 1.25 millimeters (mm) and an inside diameter of 0.5 mm, with a wall thickness of 0.375 mm. The catheter 20 may be, e.g., 50 centimeters (cm) long to reach from, e.g., a drug infusion pump implanted in the patient's abdomen to the spine.

FIG. 3 depicts catheter 20 positioned within a schematic representation of a spinal canal 30. The spinal canal 30 includes the spinal column 32 which terminates at the cauda equina 34. Also depicted is the dura 36 which contains the cerebrospinal fluid (CSF) that surrounds the spinal column 32. The catheter 20 is positioned such that the distal end 24 of the catheter 20 is located within the volume occupied by the CSF.

In the embodiment depicted in FIGS. 2 & 3, the catheter 20 includes only one opening 28 at the distal end 24 of the catheter 20. As a result, drugs delivered to the CSF through catheter 20 will exit through the opening 28 in the distal end 24 of the catheter 20. If the density of the drug so delivered is lighter than the CSF into which the drug is delivered, then the drug may form a plume 40 as seen in FIG. 3 in which the drug rises from the delivery point.

Figure 4:
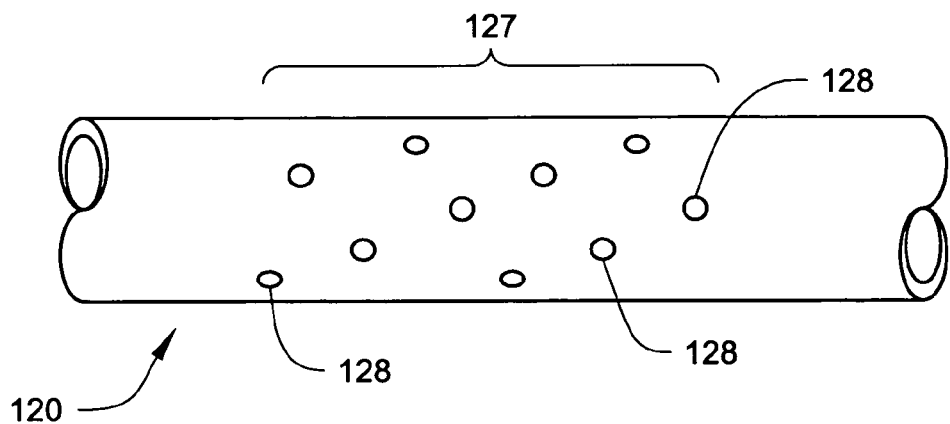
FIG. 4 is an enlarged cross-sectional view of one example of an infusion section including multiple infusion openings in a catheter used in connection with the present invention.

Many alternatives may be provided for the structure through which the drug passes out of the catheter. The catheter 20 including an opening 28 at its distal end 24 is only one example. FIG. 4 depicts a section of one alternative design in which the catheter 120 includes multiple openings 128 formed through the wall of the catheter 120 within an infusion section 127. As drug moves through the lumen of the catheter 120, it exits through the openings 128. In such an embodiment, it may be preferred that the distal end of the catheter 120 be closed such that the drug exits through openings 128 in the catheter wall. The size and spacing of the openings 128 may vary depending on a variety of factors such as, e.g., viscosity of the drug being delivered, desired delivery rate, etc.

The axial length of the infusion section 127 (as measured along an axis extending from the proximal to the distal end of the catheter) may be selected based on a variety of factors. For example, to control pain, the pain signals can be blocked by appropriate analgesic drugs in the dorsal nerve roots or in the spinal cord. Nerve roots do not have a single junction with nerve cells in the spinal cord, but split into many branches in both directions. To block a substantial number of pain signals, the drug may preferably be delivered over several vertebral levels above and below the affected nerve root. As an example, the infusion section may be constructed to cover three vertebral levels, e.g., the affected nerve root entry level and one vertebral level above and below. Each vertebral segment in a human adult is approximately 40 mm long, and, as a result, the infusion section could be, e.g., 80 mm long.

The length of infusion section 127 over which the openings 128 are dispersed may, in some embodiments, preferably have a limited axial length of, e.g., 320 millimeters (mm) or less, in some instances 160 mm or less, or even 120 mm or less. At the lower end of the range, it may be preferred that the infusion section 127 have an axial length of 20 mm or more, possibly 40 mm or more.

Figure 5:
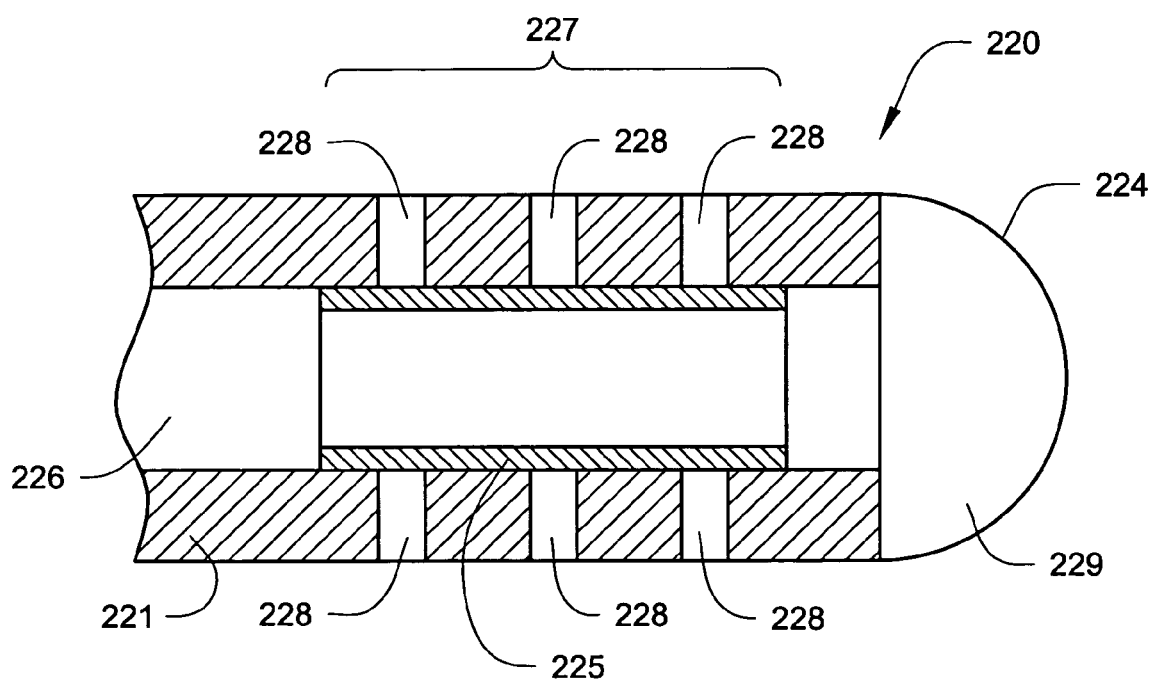
FIG. 5 is an enlarged cross-sectional view of another example of an infusion section including a permeable membrane in a catheter used in connection with the present invention.

FIG. 5 depicts another potential construction for the infusion section 227 of a catheter 220 in an enlarged cross-sectional view. The depicted infusion section 227 includes openings 228 formed in the lumen 226, e.g., through the wall 221 of the catheter 220. The distal end 224 of the catheter 220 may preferably include a plug 229 or be closed in some other manner.

Unlike catheter 120 depicted in FIG. 4, infusion section 227 of catheter 220 includes a permeable membrane 225 through which any drugs passing out of catheter 220 must pass. The permeable membrane 225 may be provided as seen in FIG. 5, e.g., as a hollow tube located within lumen 226 of the catheter 220 that is positioned to cover openings 228 such that any drug must pass through the permeable membrane before passing through openings 228. Alternative constructions could include a permeable membrane over the outside of the catheter or plugs of a permeable membrane located within the openings themselves.

In the depicted configuration, the tubing of the catheter 220 may preferably provide mechanical support for the permeable membrane 225 and may also preferably provide protection from damage for the permeable membrane 225.

The permeable membrane 225 may preferably be provided in the form of a hollow fiber similar to those used in, e.g., blood oxygenators or kidney dialysis systems. Hollow fiber permeable membranes may be made from a number of different materials that preferably do not chemically interact with the drugs to be delivered and are biocompatible, e.g., polyurethane, silicone rubber, polyimide, polyethylene, polysulfone, or polyethersulfone.

In the depicted embodiment, the outside diameter of the hollow fiber permeable membrane 225 may be the same as the inside diameter of the catheter lumen 226 such that the permeable membrane 225 may be retained in the selected location by friction that may be developed, e.g., when the catheter lumen 226 dries after swelling in a suitable swelling agent (e.g., heptane, hexane, alcohol, etc.). Alternatively, the permeable membrane 225 may be held in place by any other suitable technique or techniques, e.g., adhesives, thermal welding, chemical welding, etc. Furthermore, although the depicted permeable membrane 225 is provided in the form of a hollow fiber, the permeable membrane 225 may be provided in any other suitable form, e.g., a plug occupying the lumen 226, sheet, etc.

The openings 228 within the infusion section may be arranged in any desired manner, e.g., linearly along the axis of the catheter 220, in a spiral around the axis, a series of circumferential circles, etc. Locating the openings 228 on one side of the catheter 220 may be beneficial in, e.g., distributing the drug as described herein. As one example, the infusion openings may be, e.g., 0.05 mm in diameter, with, e.g., ten to twenty holes distributed over the infusion section 227.

As compared to spinal catheters with one or multiple infusion openings as depicted in FIGS. 2 and 4, a spinal catheter 220 having a permeable membrane 225 may offer a number of potential advantages. For example, if the pump used to deliver drug through a catheter having an infusion section with multiple holes and no permeable membrane is programmed to deliver the drug at a low rate (e.g., 0.5 milliliters (ml) per day), the drug may exit only through a single infusion opening, typically the opening that is closest to the pump. This may occur because the infusion openings are so large that no back pressure is built up in the catheter at the low infusion rates to force the infusate to reach all of the holes.

If, however, a permeable membrane 225 with sufficiently small pore sizes is used, a back pressure of drug may be built up in the catheter lumen 226 that is large enough to distribute the drug over the entire length of the infusion section 227 such that the drug passes through all of the openings 228 in the infusion section 227.

In one manner of characterizing some catheters of the present invention, the openings 228 and the permeable membrane 225 covering them within the infusion section 227 may preferably create a back pressure in the lumen 226 such that the drug exits the permeable membrane 225 through all of the openings 228 in the infusion section 227 when a drug is delivered to the infusion section through the lumen 226 at a continuous rate of 1 milliliter per hour or less.

In another manner of characterizing some catheters of the present invention, the openings 228 and the permeable membrane 225 covering them within the infusion section 227 may preferably create a back pressure 300 pascals or more in the lumen when the drug is delivered to the infusion section through the lumen at a continuous rate of 2 microliters per hour. Even at such a low back pressure, the permeable membrane 225 may preferably cause the drug to pass through all of the openings within the infusion section 227 to enhance uniform delivery of the drug over the infusion section 227.

The permeable membrane (whether in the form of a hollow fiber or some other shape) may be provided with a variety of pore sizes. The membrane pore size may be characterized in terms of Molecular Weight Cutoff (MWCO), typically the largest size molecule that will pass through the membrane. More specifically, MWCO of a permeable membrane refers to a membrane through which 90% of a substance having a particular molecular weight can pass under certain test conditions. That is, a membrane through which 90% of a permeate having a molecular weight of 80 kDa passes would be determined to have a MWCO of 80 kDa. Permeates useful for determining molecular weight cutoff include dextran T-fractions and albumin. The amount of permeate that passes through a membrane may be determined by comparing HPLC data regarding a solution containing the permeate before being applied to the membrane and after passing the membrane. HPLC analysis is useful because a calibration cure of elution time versus molecular mass may be produced. Thus, the amount and molecular weight of permeate passing through the membrane may be determined by comparison to the calibration curve. This method of measurement is typically used by filter manufacturers for filter pore sizes smaller than 0.1 micrometer (μm). In connection with the present invention, it has been found experimentally that a permeable membrane with a molecular weight cutoff of 80,000 Daltons or less may preferably be used to achieve the desired infusion characteristics.

When characterized in terms of back pressure developed within the lumen, it may be preferred that the back pressures and/or flow rates are for drug solutions that may preferably have, e.g., a viscosity of water or higher at, e.g., basal body temperatures or the temperatures at which the drug solutions are delivered.

In addition to generating the desired back pressure, permeable membranes with these pore sizes may preferably cause the drug exiting the catheter to form droplets that may preferably be small enough to be rapidly diluted into, e.g., CSF and form a diffuse cloud at the infusion site. Suitable hollow fiber permeable membranes may be obtained from, e.g., Minntech Corporation (Minneapolis, Minn.), Spectrum Laboratories, Inc. (Rancho Dominguez, Calif.), Membrana GmbH (Wuppertal, Germany), etc.

One method of manufacturing a catheter 220 with an infusion section 227 including a hollow fiber permeable membrane 225 as seen in, e.g., FIG. 5 may involve inserting the hollow fiber permeable membrane 225 in the lumen 226 of the catheter 220 and retaining the membrane 225 in position with friction. In one method of providing a friction fit, the hollow fiber 225 may have an outside diameter that is slightly larger than the inside diameter of the lumen 226, e.g., the hollow fiber 225 may have an outside diameter of 0.6 mm to fit inside a lumen with an inside diameter of 0.5 mm. If the catheter 220 is manufactured of, e.g., silicone, polyurethane, etc., the lumen 226 may be temporarily swelled by soaking in, e.g., ethyl alcohol. While the lumen 226 is swollen, the hollow fiber 225 may be placed in the lumen 226. As the alcohol evaporates out of the tubing used for catheter 220, the tubing will shrink to its original dimensions, preferably holding the hollow fiber permeable membrane 225 in position by frictional forces.

Figure 6:
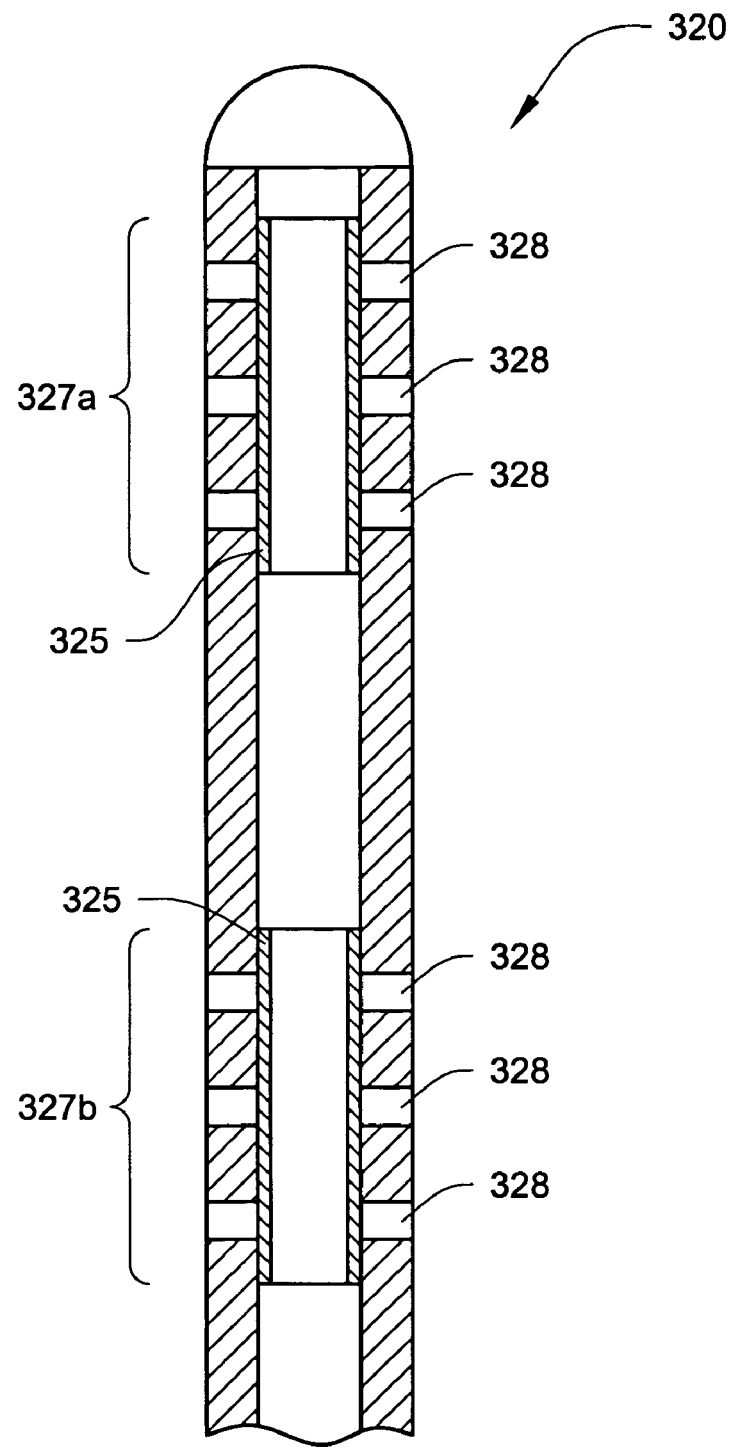
FIG. 6 depicts a catheter including two infusion sections spaced apart along the axial length of the catheter.

Another optional feature that may be provided in connection with the present invention is depicted in the cross-sectional view of FIG. 6. The catheter 320 includes two separate infusion sections 327a and 327b (collectively referred to herein as "infusion sections 327") spaced apart from each other along the axial length of the catheter 320. As discussed herein, the spacing between separate infusion sections is measured between the ends of the infusion sections 327a and 327b. In the case of infusion sections that include openings such as depicted in FIG. 6, the ends of the infusion sections are determined by the openings 328 in the two different infusion sections. For example, the spacing of the infusion sections 327a and 327b in FIG. 6 would be determined by the lowermost opening 328 in infusion section 327a and the uppermost opening 328 in infusion section 327b. It may be preferred that the lumen is impermeable to liquids between any successive pair of infusion sections such as infusion sections 327.

It should be noted that catheters according to the present invention that include two or more infusion sections may preferably include at least two such infusion sections, e.g., infusion sections 327, along one axial length of an elongate body as seen in FIG. 6 such that at least one infusion section is located between another infusion section and the proximal end of the body on which the infusion sections are located. This is in contrast to, e.g., previously known branched catheters in which each branch contains one infusion section, such that any one of the axial lengths defined by such a catheter includes only one infusion section (see, e.g., International Publication No. WO 02/07810 A2 (Elsberry et al.)) with no infusion sections located between the proximal end of the catheter and another infusion section.

The axial distance between the different infusion sections 327 may be selected based on a variety of factors such as, e.g., the distance between anatomical features to which a drug is to be delivered. For example, it may be preferred that the infusion sections 327 be separated by the distance of one human vertebral segment (e.g., 40 mm) or more. In some instances, it may be preferred that the infusion sections be spaced apart from each other by an axial distance that is a whole number multiple of one average human vertebral level (e.g., 40 mm).

Each of the infusion sections 327 may preferably include a permeable membrane 325 and one or more infusion openings 328. Because the infusion sections 327 are displaced from each other, it may be preferred to use separate permeable membranes 325 in each of the infusion sections 327. The separate permeable membranes 325 may have the same or different physical properties (e.g., MWCO values, materials, etc.) In some instances, however, a single unitary permeable membrane may extend between different infusion sections 327. Also, although FIG. 6 depicts only two infusion sections 327, it will be understood that catheters of the present invention may include more than two separate infusion sections, e.g., three or more infusion sections.

As for one potential use for a catheter having more than one infusion section, a patient may have chronic pain symptoms from more than one cause or in more than one location. For such a patient, it may be desirable to deliver analgesic drugs in more than one location along the spinal cord to reach all appropriate synapses. For example, one infusion section could be located proximate the spinal cord at a higher vertebral level, so that the drug will preferably reach receptors at different vertebral levels.

Figure 7:
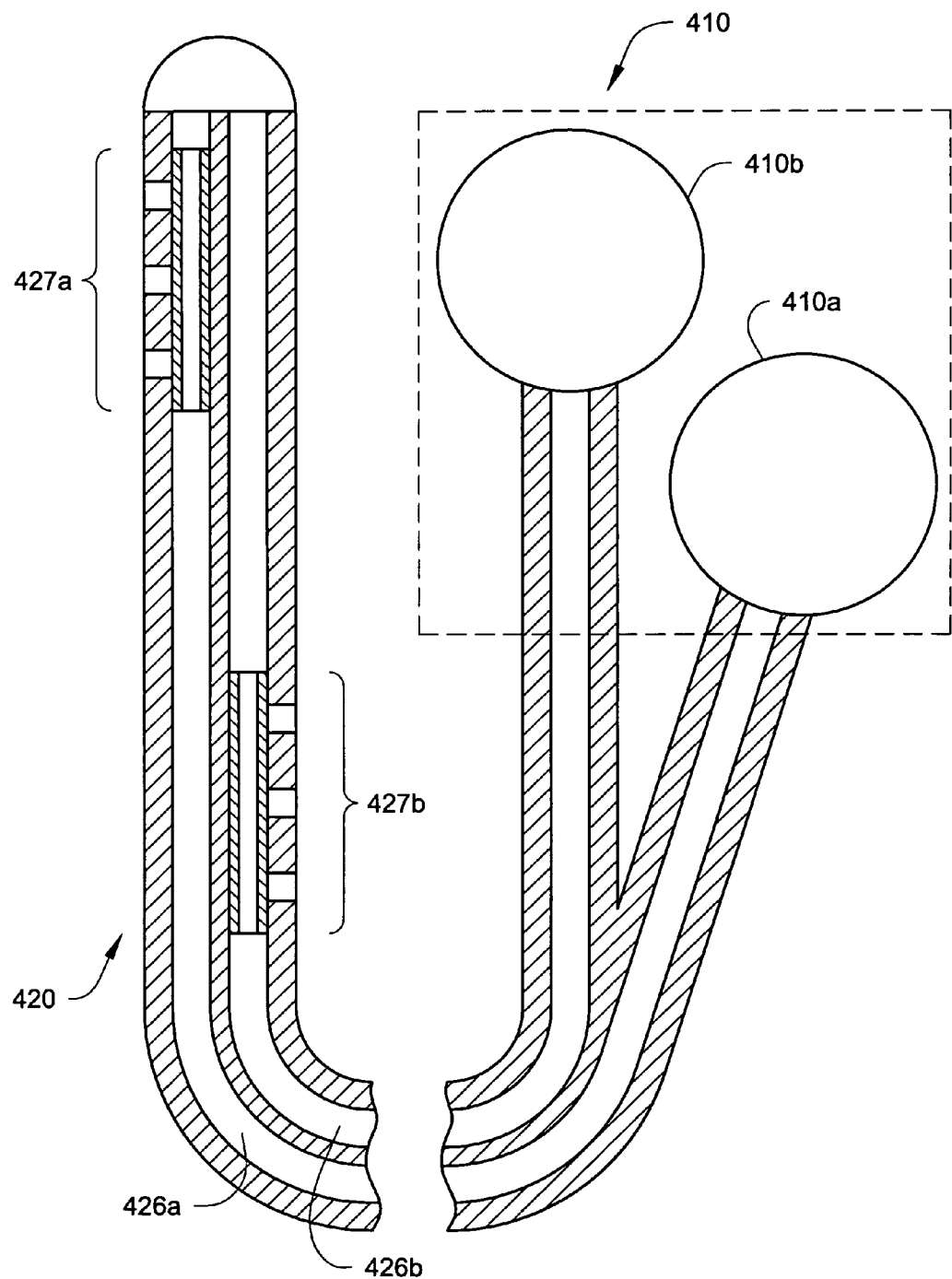
FIG. 7 depicts another drug infusion system according to the present invention including a catheter with two lumens and two pump mechanisms.

Still another drug delivery system that may be used in connection with the present invention is depicted in FIG. 7. The catheter 420 (depicted in cross-section) includes two infusion sections 427a and 427b (collectively referred to herein as "infusion sections 427"). Unlike catheter 320 of FIG. 6 in which a single lumen services both infusion sections 327, however, each of the infusions sections 427 of catheter 420 is serviced by a separate lumen 426a or 426b.

Even though serviced by separate lumens 426a and 426b, however, the infusion sections 427 can still be characterized as including one section 427b that is located between the proximal end of the catheter 420 (i.e., the end attached to pump assembly 410) and the other infusion section 427b along the axial length of the body of the catheter 420.

In such an embodiment, the catheter 420 may be used to, e.g., deliver two different drugs to different locations along the length of the catheter 420 (the different locations being identified by the location of the different infusion sections 427). Alternatively, the catheter 420 may be used to deliver the same drug to two different locations at different times and/or for different periods of time. It will be understood that although only two lumens and infusion sections are depicted, devices and methods of the present invention may involve catheters with three or more lumens, three or more infusion sections and associated pump assemblies.

Also, although two infusion sections 427 and two lumens 426a and 426b are depicted in connection with the embodiment of FIG. 7, it will be understood that catheters of the present invention may include more than two infusion sections and/or more than two lumens to service the different infusion sections. Although not depicted, for example, one (or both) of the infusion sections 427 could be serviced by two or more separate lumens such that two or more different drugs could be delivered by the same infusion section at the same or different times. For example, infusion section 427a could be serviced by two lumens in place of the single lumen 426a depicted in FIG. 7.

A schematic diagram of one pump assembly 410 that may be used in connection with a catheter 420 is seen in FIG. 7. The pump assembly 410 may include, e.g., multiple pump mechanisms 410a and 410b that are, respectively, preferably connected to lumens 426a and 426b. Such a system may be useful if the two different pump mechanisms 410a and 410b are to be operated independent of each other. In some other systems, it may be sufficient to provide a single pump mechanism including two or more reservoirs with different drug solutions. In such a system, the reservoirs may be dedicated to a particular lumen or a switching valve assembly may be used to deliver drug solution from either reservoir to either or both of the lumens 426a and 426b as desired.

Among the methods of the present invention, it may be beneficial to exploit the natural tendencies of liquids to move relative to each other in response to gravitational and other forces. For example, because humans sit and stand in an upright position when awake, drugs delivered to the CSF may rise or fall in the spinal canal due to buoyancy. Buoyant forces may move the drug more rapidly than diffusion processes cause the drug to spread radially. Drugs that are more dense than CSF may tend to fall (i.e., move towards the cauda equina) and drugs that are less dense than CSF will rise (towards, e.g., the brain). Density of fluids may be described in terms of baricity. Drugs (or solutions carrying the drugs) may be described relative to the CSF of a patient as being hypobaric (e.g., less dense than CSF and, therefore, tending to rise in CSF) or hyperbaric (e.g., more dense than CSF and, therefore, tending to fall in CSF). The drug may also be described as isobaric (e.g., have neutral baricity, i.e., the same density as CSF) and, therefore, neither tending to rise or fall within the CSF.

Thus, if a patient is not responding to a particular therapy because a catheter is delivering a drug to a location that is too high in the spinal column, a drug solution having an increased density may be introduced to allow the drug to drop to a level of the spinal column where the drug may be more effective in treating the patient. If a patient is not responding to a particular therapy because a catheter is placed too low in the spinal column, a drug solution having decreased density may be introduced to allow the drug to rise to a level of the spinal column where the drug may be more effective in treating the patient. The catheter may also be repositioned to more effectively deliver the drug to a more desired region of the spinal cord.

If it is desired to have a drug reach a selected region of a spinal cord in roughly proportional concentrations across the particular region, it may be desirable to infuse the drug through a permeable membrane such that the drug may readily mix with CSF and diffuse throughout the particular region in roughly equal concentrations.

In some methods according to the present invention, the density of the drug solution may be adjusted before the drug solution is delivered to the pump apparatus. In such a system the density of the patient's CSF may be known (within a range of biologically expected values) or the actual density of the CSF may be determined by, e.g., drawing a sample and determining the density of the sample. The density of the drug solution may be adjusted relative to the expected or measured density of the CSF and a drug solution with a selected density can be supplied in the pump apparatus for delivery to the CSF by infusion.

In a variation on the above example, a system may be supplied that includes the same drug in two or more different solutions that have different densities relative to the density of the CSF. Referring to, e.g., FIG. 7, the two pump mechanisms 410a and 410b may be loaded with the same drug in solutions having two different densities. As a result, the same drug may be delivered to the CSF with different densities based on, e.g., the measured density of the patient's CSF, a desired distribution profile, etc. The different drug solutions may be delivered to either of the infusion sections 427a and/or 427b as desired.

In one variation on this method, different drug solutions with same or different densities may also be supplied in the reservoirs of each of the different pump mechanisms 410a and 410b. For example, it may be desirable to use more than one analgesic drug to treat multiple types of pain. For example, nociceptive pain, caused by stimulation of neurosensors, will typically respond to an opioid such as morphine, but neuropathic pain caused by damage to nerve cells will typically respond better to a local anesthetic such as BUPIVACAINE. One method of combining more than one drug is to simply mix them in the reservoir of an implantable drug pump and infuse the mixture through a catheter.

In some cases, however, it may be preferred to deliver the different drugs separately to different locations. The system of FIG. 7 may be used to accomplish this method because catheter 420 has two separate lumens 426a and 426b and separate infusion sections 427a and 427b at different locations on the catheter 420. For example, BUPIVACAINE could be infused through the first lumen 426a such that it is infused proximate the lumbar nerve roots. A second drug, e.g. morphine, may be infused through the second lumen 426b at, e.g., a location proximate the spinal cord at a higher vertebral level, so that the drug will preferably diffuse to the dorsal horn which is at a higher, thoracic level in the spinal canal.

Although it may be beneficial to use a system in which one or more drug solutions are formulated outside of the patient to have a selected density, it may be beneficial to mix or formulate drug solutions having selected densities on-board the pump assembly. By mixing the drug solutions on-board the pump assembly (which may preferably be implanted in the body of the patient), a level of control may be achieved that is not possible in known systems.

Figure 8:
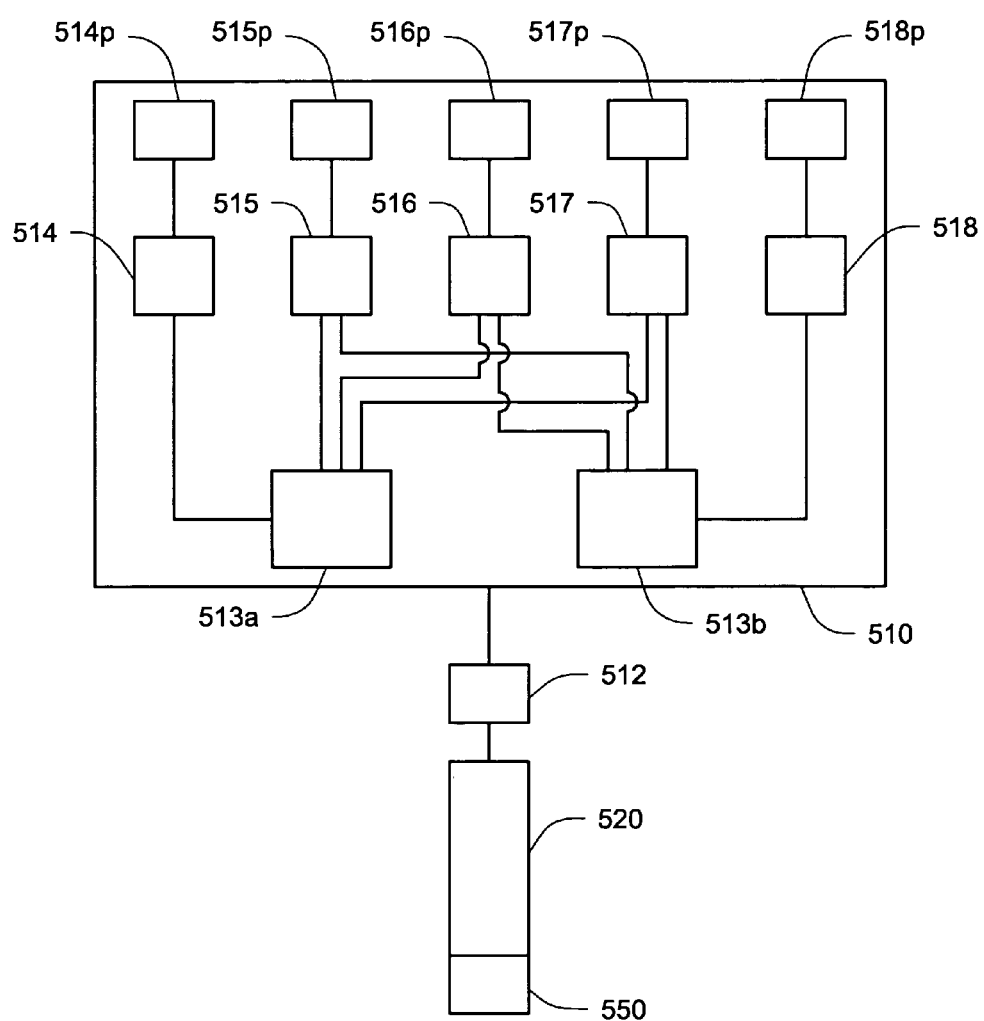
FIG. 8 is a schematic diagram of another drug delivery system according to the present invention including multiple reservoirs for mixing drug solutions with selected densities or other properties.

One exemplary pump assembly 510 that may be used in connection with the present invention to take advantage of the buoyant forces to achieve some desired drug distribution profile is depicted in FIG. 8 (as a schematic block diagram for simplicity). The pump apparatus 510 includes a connector 512 for connection to a catheter 520. The catheter 520 may preferably include one or more lumens that each feed one or more infusion sections 527a and 527b as discussed herein.

The depicted pump apparatus 510 includes multiple reservoirs 514, 515, 516, 517, and 518. The reservoirs 514, 515, 516, 517, and 518 may contain the same fluids or different fluids, although it may be preferred that at least one of the reservoirs contain at least one drug for delivery to the patient. The other reservoirs may contain fluids that are designed to allow the user to manipulate the density of the drug solution delivered through the catheter. For example, reservoir 515 may contain a hypobaric liquid (e.g., water), reservoir 516 may contain a hyperbaric liquid (e.g., glucose solution), and reservoir 517 may contain a neutral liquid (e.g., saline). When combined with, e.g., a first drug in reservoir 514 in various fractions, the density of the drug solution delivered through the catheter 520 can be adjusted to achieve a desired density or baricity with respect to the CSF. Similarly, reservoir 518 may include, e.g., a second drug that may also be delivered to the catheter 520 in selected densities. In still other variations, two or more of the reservoirs may contain the same drug, but in solutions having different densities.

The depicted pump apparatus 510 includes optional means for mixing 513a and 513b to mix the various components of the drug solutions before delivery to the connector 512 and attached catheter 520. The means for mixing 513a and 513b may be provided in a variety of forms, e.g., as mixing chambers, mechanical agitators, vibrating components, static mixers, etc, and combinations thereof. In another alternative, the velocity at which the components are delivered to, e.g., the means for mixing 513a and 513b, the connector 512, and/or the catheter 520 may be increased to enhance mixing. Furthermore, the means for mixing may be incorporated into the catheter 520 itself.

Each of the reservoirs may also preferably be operably connected to a refilling port 514p, 515p, 516p, 517p, and 518p such that the different reservoirs can be refilled. The ports may be located in one common septum or in different septums at different locations on the body of the pump apparatus. A variety of techniques may be used to ensure refilling of the selected reservoir. For example, the ports may accept differently sized or shaped needles, the ports may be located in known positions and a template may be placed on the patient's skin to assist in refilling, etc.

By providing a variety of drugs and liquids as in pump apparatus 510, the density of the drug solutions delivered to the CSF may be adjusted to, e.g., mix a drug solution that is isobaric (i.e., neutral density) with respect to the CSF, mix a drug solution that is hyperbaric (i.e., less dense) as compared to the CSF, and mix a drug solution that is hypobaric (i.e., more dense) as compared to the CSF. Furthermore, the density of the drug solution can be adjusted during delivery, i.e., it may be changed to adjust to changes in the density of the CSF and/or to achieve a desired density profile. For example, a hyperbaric drug solution may be delivered followed by delivery of a hypobaric drug solution (or vice versa) to deliver drug over a wider region of the spinal canal.

Where the pump apparatus 510 includes two different drugs, it will be understood that a similar system could be provided that includes only one drug. Other variations may be provided in catheter 520 which may include, e.g., one or more lumens, one or more infusion sections, etc.

One optional feature that is depicted in connection with FIG. 8 is that catheter 520 may include a density sensor 550 such that the actual density of the CSF may be measured. Density sensors may be manufactured using, e.g., microelectromechanical sensor (MEMS) technology in the form of a beam or float configuration. See, e.g., Costello et al., "Density and Viscosity Sensing with Ultrasonic Flexural Plate Waves," Proceedings of Transducers '93, 7$^{th}$ International Conference on Solid-State Sensors and Actuators, Yokohama, Japan, June 1993, Institute of Electrical Engineers, Japan, pp. 704-707. Such devices may be incorporated in the delivery catheter 520 as depicted or, alternatively, a separate device may be located in the CSF to measure CSF density.

If the actual density of the CSF is measured, that information can be fed back into the pump assembly 510 such that the formulation of the drug solution or solutions can be adjusted to achieve a desired density relative to the CSF density. Such measurements and/or adjustments may be made continuously or at different times as desired using, e.g., open loop or closed loop control systems and methods.

In spite of the density of the drugs as discussed above, drugs may be delivered to the CSF in a manner that results in essentially neutral buoyancy even though the drug itself may be hypobaric or hyperbaric with respect to CSF. For example, if a permeable membrane is used to deliver the drug, the droplets or particles of drug exiting from the membrane may be so small as to result in a drug-CSF mixture that has a density close to pure CSF, thus reducing buoyant forces on the drug. The drug may then remain in the area of infusion, and diffusion will expand the drug into a cloud radially.

It should also be understood that although buoyant forces may play a role in drug movement and/or diffusion, the CSF itself is undergoing oscillation and bulk flow that may sometimes overcome the effects of baricity, e.g., causing hyperbaric drugs to rise and/or hypobaric drugs to fall in the spinal column.

Other factors that may play a role in the diffusion of drugs within the spinal canal include, e.g., the rate of infusion, drug distribution patterns between the different compartments of the spinal canal, whether the drugs are hydrophilic or lipophilic, the temperature of the drug at the time of infusion, etc.

With respect to the rate of infusion, low rates of infusion may tend to yield more equitable drug distribution radially for both hypobaric and hyperbaric drugs. Faster flow rates may lead to broader drug distribution over more vertebral segments than slower flow rates. As such, if it is desirable to reach a variety of levels of a spinal column with drug, the flow rate with which the drug is delivered may be increased. In such circumstances, it may be desirable to decrease the concentration of a drug to be delivered. If it is desired to have a drug localized to a region around a particular level of the spinal column, the flow rate with which the drug is delivered may be decreased. In such circumstances it may be desirable to increase the concentration of the drug within the solution delivered through the catheter.

It may also be desirable to infuse a drug in discrete intervals in which a bolus of drug is delivered followed by an interval in which little or no drug is delivered through the catheter (as opposed to a continuous delivery infusion). Such non-continuous delivery modes may also be useful to modify the distribution profile of a drug within the spinal column.

In addition, bolus or non-continuous delivery of a drug may provide other advantages in the management of the body's response to infusion of a drug. For example, such a delivery method may be helpful in reducing the incidence of inflammatory masses at the infusion site. Inflammatory mass is related to local drug concentration in the spinal canal. In particular, the systems and methods of the present invention may be helpful in addressing this issue because the site at which the drug is delivered may be periodically changed (using, e.g., multiple infusion sites). In addition, by adjusting the density of the drug solution, various distribution profiles for the infused drug may be obtained that could reduce the incidence of inflammatory masses (e.g., alternating between hypobaric and hyperbaric drug solutions). Also, systems that deliver two or more different drugs may also be used to address the incidence of inflammatory masses by alternating delivery between the different drugs to ameliorate the inflammatory response to continuous delivery of the same drug. Still another manner by which the catheters, systems and methods of the present invention may reduce inflammatory masses is by reducing drug density in e.g., CSF or other fluids, for drugs passed through a permeable membrane during delivery (which can reduce the size of any one droplet of the drug by the relatively small pore sizes of the permeable membranes). In addition, delivering a drug over a wider field, through the use of e.g. a catheter with a wide infusion section covered by a permeable membrane catheter, will serve to reduce the local drug concentration.

As noted above, drug distribution patterns between the different compartments of the spinal canal may also be considered in connection with the present invention. In some instances, it may be desirable to place the infusion section or sections of the catheter in one or more selected locations in the spinal region.

The spinal canal is, however, not an open channel, but has several structures that divide the canal into separate channels. The dorsal nerve roots, ventral nerve roots, dentate ligaments, and septum posticum are typically present over the length of the spinal cord. They can act as barriers to even distribution of a drug around the circumference of the spinal cord. As a result, it may be desirable to locate an infusion section on a catheter in, e.g., a dorsal location, ventral location, etc. with respect to, e.g., the spinal cord.

For example, sensory signals, including pain signals, are transmitted into the spinal cord through the dorsal roots. The first synapse is located in the dorsal horn. It may be preferred, e.g., to locate an infusion section of a catheter on the dorsal side of the spinal cord to get the most drug (e.g., an analgesic drug) into the synapses in the dorsal horn. Motor signals are transmitted out through the ventral roots. Movement disorders may be controlled by enhancing the excitatory or inhibitory signals from the brain before the signals are transmitted to the ventral roots. In this case, it may be desirable to locate the catheter on the ventral side of the spinal cord and get the most drug into the ventral synapses.

Catheters of the present invention may, e.g., be inserted into the spinal region at a level below the end of the spinal cord and then threaded up to the desired level. The catheters may, however, be very limp, making it difficult or impossible to steer the catheter into a specific area of the spinal region. A guidewire may be used to stiffen the catheter during placement. The guidewire is then typically removed before the catheter is used to infuse drugs. The catheters of the present invention may include a guidewire lumen to receive the guidewire.

The catheter itself and/or a guidewire used with the catheter may preferably be steerable so that the catheter can be guided in a specific direction within the spinal region or other body location of interest. Some potentially suitable steerable catheters including guidewire lumens and/or steerable guidewires may be described in, e.g., U.S. Pat. No. 4,811,743 (Stevens); U.S. Pat. No. 4,815,478 (Buchbinder et al.); U.S. Pat. No. 5,003,989 (Taylor et al.); U.S. Pat. No. 5,195,965 (Lundquist et al.); U.S. Pat. No. 5,395,328 (Ockuly et al.); U.S. Pat. No. 5,397,304 (Truckai); U.S. Pat. No. 5,415,633 (Lazarus et al.); U.S. Pat. No. 5,480,382 (Hammerslag et al.); U.S. Pat. No. 6,059,739 (Baumann); U.S. Pat. No. 6,371,929 (Steele); U.S. Pat. No. 6,485,440 (Gardeski); U.S. Pat. No. 6,500,130 (Kinsella et al.); U.S. Pat. No. 6,512,957 (Witte); and U.S. Pat. No. 6,607,496 (Poor et al.). Steerable catheters and/or guidewires used in connection with the present invention may take any suitable construction, e.g., bent tip, thermally actuated, pull-wire controlled, etc. The entire disclosure of each of the documents identified in this paragraph are hereby incorporated by reference.

A variety of techniques may be used to track the location and/or direction of the catheter, components on the catheter (e.g., infusion sections, etc.) and/or guidewire during placement. These tracking techniques may include, e.g., fluoroscopically, ultrasonically, electrical conductivity, optically, electromagnetically, etc. Some potentially suitable methods and systems for tracking may be described in, e.g., U.S. Pat. No. 3,868,565 (Kuipers); U.S. Pat. No. 4,173,228 (Van Steenwyk et al.); U.S. Pat. No. 4,317,078 (Weed et al.); U.S. Pat. No. 4,642,786 (Hansen); U.S. Pat. No. 4,821,731 (Martinelli et al.); U.S. Pat. No. 4,905,698 (Strohl, Jr. et al.); U.S. Pat. No. 5,211,165 (Dumoulin et al.); U.S. Pat. No. 5,592,939 (Martinelli); U.S. Pat. No. 5,697,377 (Wittkampf); U.S. Pat. No. 5,913,820 (Bladen et al.); U.S. Pat. No. 6,379,302 (Kessman et al.); U.S. Pat. No. 6,381,485 (Hunter et al.); U.S. Pat. No. 6,434,507 (Clayton et al.); U.S. Pat. No. 6,474,341 (Hunter et al.); and U.S. Pat. No. 6,636,757 (Jascob et al.). Other potentially suitable methods and systems may be described in European Patent Application Nos. EP 1 391 181 A1 (Verard et al.); and EP 1 421 913 A1 (Hunter et al.). Still other potentially suitable methods and systems may be described in International Publication Nos. WO 94/04938 (Bladen et al.); WO 96/11624 (Bucholz et al.); WO 99/33406 (Hunter et al.); WO 00/56215 A1 (Foley et al.); WO 00/64367 (Melkent et al.) WO 01/34050 A3 (Hunter et al.); WO 01/64124 (Melkent et al.); and WO 01/76497 (Simon et al.). The entire disclosure of each of the documents identified in this paragraph are hereby incorporated by reference.

Figure 13:
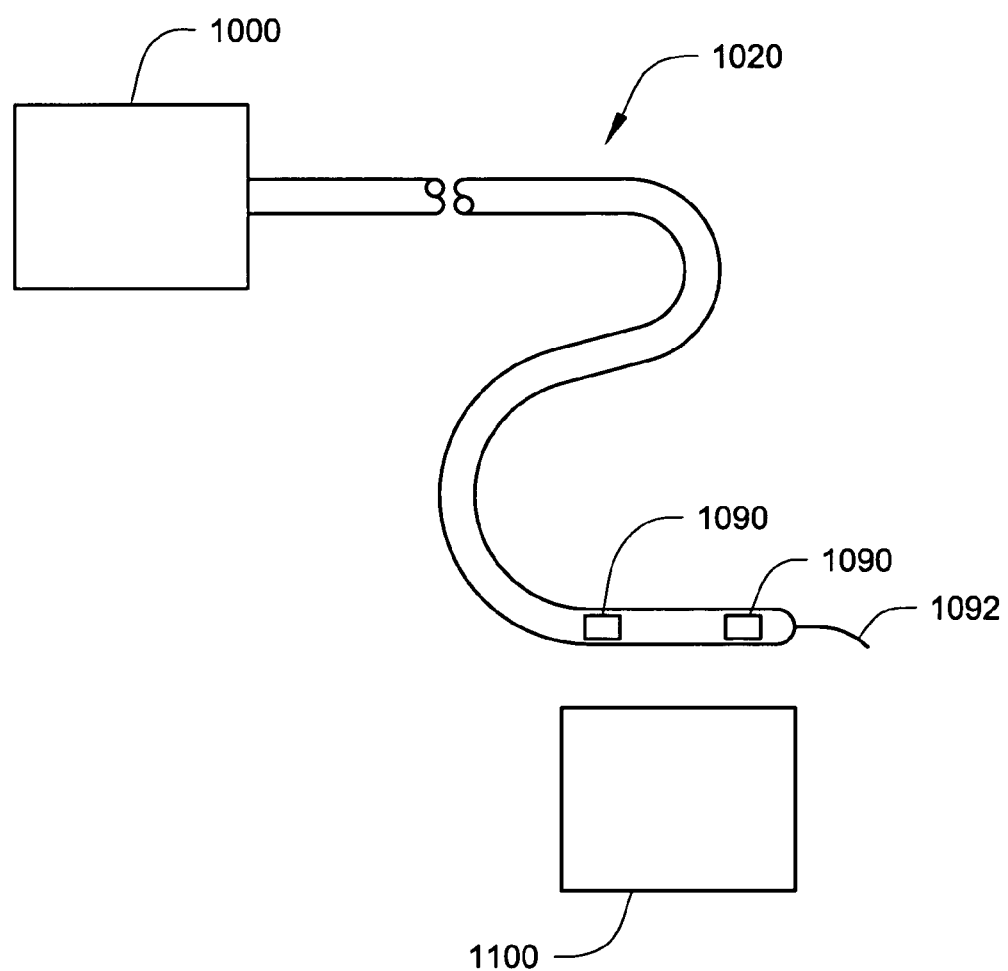
FIG. 13 depicts a catheter according to the present invention attached to a delivery/reservoir and which includes two tracking elements.

FIG. 13 depicts one potential system including a catheter that may be used in connection with the present invention. The catheter 1020 is preferably attached to a fluid delivery/reservoir 1000 as described herein. The catheter may include one or more infusion sections that are fed by one or more lumens as also described herein. The infusion sections may preferably include a permeable membrane as described herein. The catheter 1020 includes two tracking elements 1090 attached to the elongated body of the catheter 1020. The tracking elements 1090 are preferably in a construction suitable for the tracking system 1100 to use in determining the position of the tracking elements 1090 when the catheter 1020 is located within the body of a subject. For example, the tracking elements 1090 may take the form of coils if the tracking system 1100 uses electromagnetic energy/fields to perform the tracking function. Other constructions may be include light reflectors/emitters if tracking is performed optically, radio-opacity if the tracking is accomplished using fluoroscopy, etc.

Generally, the tracking elements 1090 may be passive or active. A passive tracking element 1090 is one that does not actively transmit or emit energy, e.g., a reflector, an electromagnetic coil, etc. An active tracking element 1090 is one that transmits a signal or emits energy that can then be detected to determine the position of the tracking element (e.g., light emitting diodes, RF transmitters, etc.)

It may be preferred that the one or both of the tracking elements 1090 be attached to the catheter 1020 at selected locations that are proximate the same or different infusion sections to allow a practitioner to determine the position of the infusion section(s) based on the position of a tracking element. It may be preferred that two or more tracking elements be provided to offer potential redundancy in the tracking operation. In some instances where two or more tracking elements are provided, the tracking elements may operate with the same modality (e.g., they may both be coils used in an electromagnetic tracking system, both be reflectors in an optical tracking system, etc.). In an alternative, the tracking elements may operate using different modalities (e.g., one may be a coil used in an electromagnetic tracking system and another a reflector used in an optical system, etc.).

The system depicted in FIG. 13 also includes a guidewire 1092 extending from the distal end of the catheter 1020. The guidewire 1092 may preferably be located within a guidewire lumen provided in the catheter 1020. It may be preferred that the guidewire 1092 be a bent tip guidewire as depicted, although other guidewires may alternatively be used. Although not depicted because of size limitations, it may be preferred that the guidewire 1092 include one or more tracking elements attached thereto such that the position of the guidewire can be determined by a tracking system (e.g., tracking system 1100). The tracking elements on a guidewire 1092 may be in addition to tracking elements 1090 on catheter 1020 or in place of tracking elements 1090.

Methods of positioning or locating a drug delivery catheter of the present invention may include, but are not limited to, locating the catheter at least partially within the spinal region of a subject. Such a method may include, e.g., introducing the catheter 1020 into the spinal region of a subject and tracking one or more of the tracking elements 1090 on the catheter 1020 to determine the position of one or more infusion sections within the spinal region. Determining the position of the infusion sections may be accomplished directly where the tracking elements and the infusion sections are in close proximity. Alternatively, it may be possible to deduce the position of an infusion section that is located a known distance from a tracking element. The method may further include advancing the catheter 1020 into the spinal region until one or more infusion sections are at selected locations within the spinal region.

The methods may include the use of guidewires and guidewire lumens to assist in the placement of the catheter. As discussed herein, the guidewire may or may not include tracking elements of its own. Also as discussed herein, the selected location(s) for the infusion sections may be, e.g., the dorsal and/or ventral sides of the spinal cord.

Although the catheters, systems and methods of the present invention may be useful for infusing drugs to the CSF, there are other neurological applications where the present invention may be useful. One example would be to deliver drugs to other areas within the spinal region, for example, when the site of back pain can be localized to a disc, bone, muscle, or ligament in the spine, a mixture of a steroid and a local anesthetic can be delivered to reduce swelling and reduce pain. The infusion sections of catheters according to the present invention may preferably deliver drug to the entire structure, rather than delivering drug at a single point and depending on diffusion and convection to cover the entire area.

Another example would be delivering drugs into the brain. Functional areas in the brain are three-dimensional structures, not a single point. Clinical examples include delivering a chemotherapy agent to a tumor and delivering dopamine to the putamen for treatment of Parkinson's Disease. In yet another example, seizure activity in epileptic patients can be localized to a region in the thalamus or cerebral cortex. An anti-convulsant can be delivered to this region to terminate a seizure or to prevent further seizure activity. Again, a catheter with a permeable membrane may provide better organ coverage than delivering drug at a single point.

Yet another example would be a neurological disorder in a specific limb, such as an arm or leg. An example would be pain due to neuropathy caused by diabetes. The pain could be reduced by delivering a local anesthetic (and potentially a steroid) to a main trunk of the nerve that has been affected. The catheter with a permeable membrane could be surgically placed alongside the nerve, and infuse drug over a length of the nerve. The anesthetic may preferably cover a larger area of the nerve and be localized to the specific nerve, rather than deliver the drug at a point and depend on diffusion and convection to distribute the drug. FIG. 1C depicts a catheter placed next to a peripheral nerve in the arm. It should be recognized that these are only examples; other organs and disease states could also benefit from the use of this catheter.

Another drug distribution factor to consider in connection with the present invention is whether the drug is hydrophilic or lipophilic. Although not wishing to be bound by theory, it is theorized that hydrophilic drugs may have a wider distribution profile than lipophilic drugs. Accordingly, if it is desirable to reach a variety of levels of a spinal canal with a drug, it may be desirable to select and/or formulate a drug with hydrophilic properties. Alternatively, if it is desired to have a drug localized to a region around a particular level of the spinal cord, a drug having more lipophilic properties may be selected.

Figure 9:
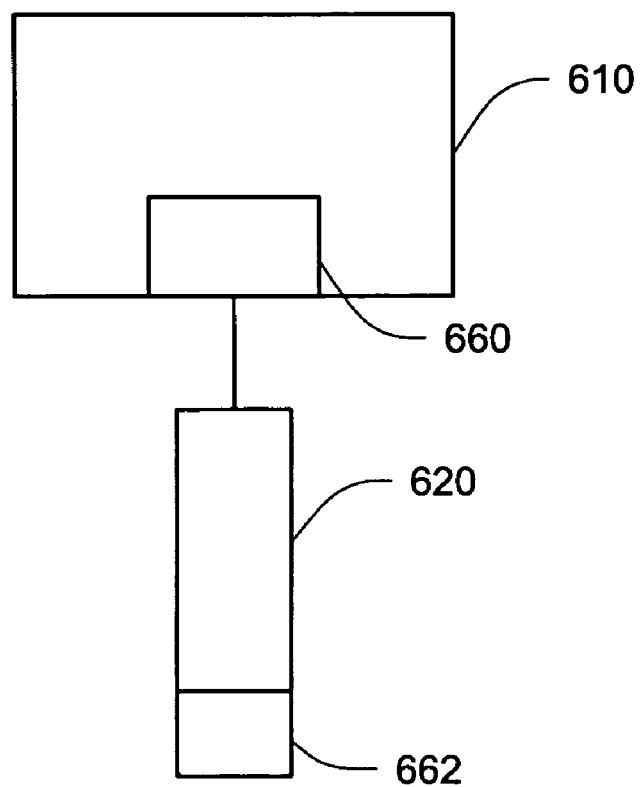
FIG. 9 is a schematic diagram of another drug delivery system including thermal control devices for controlling the temperature of the drugs delivered to the patient.

Drug distribution within the spinal canal may also be affected by controlling the temperature of the drug as delivered to the spinal canal. For example, heating the drug solution may make that solution more hypobaric (e.g., less dense) and/or cooling the drug solution may make it hyperbaric (e.g., more dense). FIG. 9 depicts a system in which the pump assembly 610 includes a thermal control device 660 to adjust the temperature of the drug solution before delivery to the catheter 620. In addition to or in place of thermal control device 660, the catheter 620 may include a thermal control device 662. Suitable thermal control devices may be, e.g., electrical resistance heaters, Peltier devices, etc.

Figure 10:
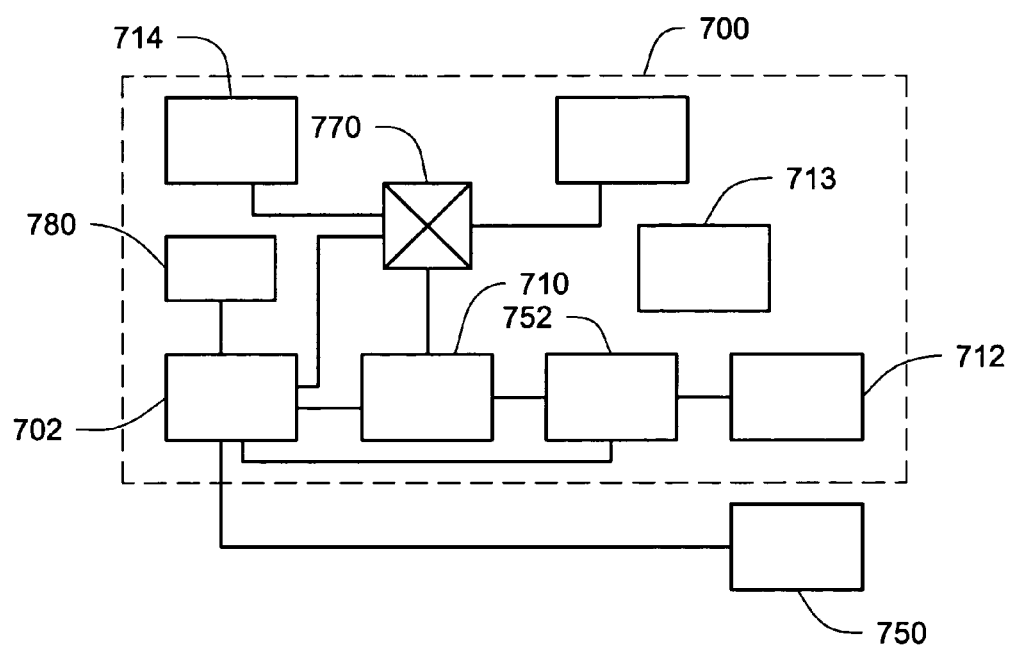
FIG. 10 is a schematic diagram of another drug delivery system according to the present invention incorporating a variety of optional components.

FIG. 10 is a schematic diagram of another drug delivery system according to the present invention. The system 700 includes a pump assembly 710 (preferably implantable), catheter connection port 712, and two reservoirs 714 and 715 (preferably implantable). The reservoirs 714 and 715 are connected to the pump assembly 710 through a reservoir switching valve assembly 770 that is capable of selectively connecting the reservoirs 714 and 715 to the port 712.

Also depicted in FIG. 10 is a controller 702 for operating one or more components of the system 700. The controller 702 may be, e.g., a microprocessor or other control device. The controller 702 is depicted as being operably connected to the pump assembly 710, reservoir switching valve assembly 770, an external density sensor 750, an internal density sensor 752, and a telemetry module 780. The controller 702 may be used to adjust the pump assembly 710 to, e.g., obtain a desired flow rate, back pressure, etc. In such a capacity, the pump assembly 710 and controller 702 may operate as a programmable pump assembly. Although controller 702 is depicted as a separate component, it will be understood that it could be incorporated into one or more of the components in the depicted system 700 (e.g., the pump assembly 710, etc.). Also, although pump assembly 710 is depicted as a single component, it will be understood that pump assembly 710 could include one, two, three, or more pump mechanisms that may be operated independently of each other.

The optional telemetry module 780 may be operatively connected to the controller 702 to provide for communication between one or more of the components in system 700 and a user, external programming device, etc. Telemetry control devices, systems and methods that may be used in connection with the present invention may be described in, e.g., U.S. Pat. No. 5,558,640 (Pfeiler et al.); U.S. Pat. No. 5,820,589 (Torgerson et al.); and U.S. Pat. No. 5,999,857 (Weijand et al.). Although telemetry module 780 is depicted as being connected to the controller 702, it will be understood that the telemetry module 780 may alternatively be connected directly to one or more of the components, e.g., the pump 710, mixing means 713, density sensors 750/752, reservoir switching valve assembly 770, etc. The telemetry control module 780 may provide for one-way or two-way communication.

An optional external density sensor 750 is depicted in connection with FIG. 10 as operably connected to the controller 702 of drug delivery system 700. The external density sensor 750 may preferably be implantable and may be used in a control loop to, e.g., provide density information such that a reservoir from which a drug is to be delivered can be selected. If implanted, it may be preferred that the external density sensor 750 be located within the fluid into which the drug or drugs are to be delivered, e.g., the CSF of a patient.

An optional internal density sensor 752 is also depicted in connection with FIG. 10 and may be used to, e.g., sense the density of the drug solution as delivered to the catheter connection port 712. Such an internal density sensor 752 may be used in, e.g., a closed loop control system in which, e.g., the density of the CSF of the patient is determined and a selected density for the drug solution to be delivered to the patient is determined. The drug solution can then be formulated from, e.g., the fluids in reservoirs 714 and 715. Before the drug solution is delivered to the patient, however, its actual density can be measured using internal density sensor 752 such that adjustments can be made (if needed) to provide a drug solution with the desired density. Such a method/system may be described as a closed loop control system/method.

Alternatively, the system may be operated in an open loop configuration. In one embodiment, the external density sensor 750 may be provided to determine the density of, e.g., the CSF and provide that information to controller 702 which can then adjust the density of the drug solution using, e.g., reservoir switching valve assembly 770. In such an open-loop system/method, an internal density sensor 752 may not be provided, with the density of the drug solution being calculated on, e.g., known or expected values of the different components in reservoirs 714 and 715.

In another embodiment of an open-loop control system/method, only an internal density sensor 752 may be provided such that the actual density of the drug solution delivered to the catheter connection port 712 can be measured and adjusted based on a desired density.

Still other embodiments of open-loop control systems and methods may be envisioned in connection with the present invention.

The system 700 may also preferably include means for mixing 713 if it is desired to mix the fluids within the reservoirs 714 and 715. The means for mixing may take any suitable form and be located in any suitable location. For example, the means for mixing 713 may be located within the valve assembly 770, pump 710, port 712 or at any other location. As discussed herein, the means for mixing 713 may take a variety of forms including both active mixing devices (e.g., mechanical agitators) and passive mixing devices (e.g., mixing chambers, static mixers, etc.). The means for mixing 713 may preferably be connected to the controller 702 as shown if control over the means for mixing 713 is desired or required during operation.

Figure 11:
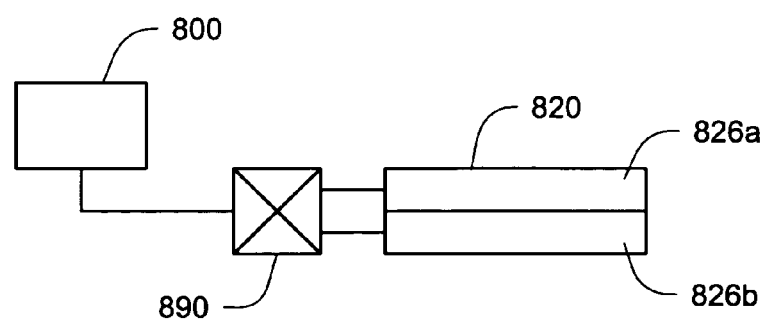
FIG. 11 is a schematic diagram of another drug delivery system according to the present invention incorporating a lumen switching valve assembly.

Yet another alternative drug delivery system according to the present invention is depicted in FIG. 11. In many respects, the system 800 may be similar to system 700 of FIG. 10. System 800 does, however, preferably include a lumen switching valve assembly 890 located between the catheter 820 and the drug delivery system 800 such that output from the system 800 can be directed into the appropriate lumen 826a and/or 826b of catheter 820. The lumen switching valve assembly 890 and the system 800 may preferably be operably connected to, e.g., a controller located within system 800 (as described in connection with, e.g., system 700 above). Also, the system 800 may preferably include a pump assembly that includes two or more independent pump mechanisms to deliver drugs to the different lumens in catheter 820 independently.

Figure 12:
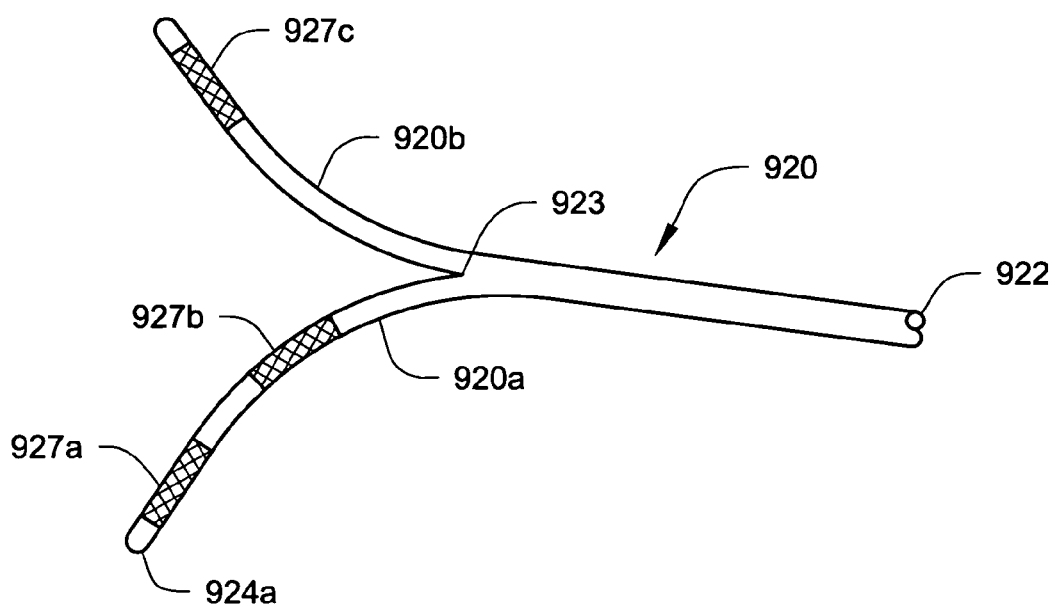
FIG. 12 depicts a catheter according to the present invention including a fork and two branches extending therefrom.

In some situations, it may be desired to infuse a drug to multiple locations that are not collinear such that they cannot be reached by a single, unbranched catheter. As an example, it may be desired to infuse the same drug into both hemispheres of the brain. To accomplish such a method, a catheter may be used that includes one or more forks (e.g., a "Y") at which the catheter splits into two or more separate branches. One example of such an embodiment is depicted in FIG. 12. The catheter 920 splits into branches 920a and 920b at fork 923.

Branch 922a includes two infusion sections 927a and 927b located along the elongated body of the branch 922a. As a result, infusion section 927b is located between the proximal end 922 of the catheter and the other infusion section 927a. Although only two infusion sections are shown along branch 920a, it will be understood that three or more infusion sections could be provided along the branch 920a or in-line with each other from the proximal end 922 to the distal end 924a of branch 920a. In some embodiments, it may be possible that an infusion section could be located along the length of the catheter 920 between the fork 923 and the proximal end 922, with one or more infusion sections located along one or both of the branches 920a and 920b.

Also, while catheter 920 includes only one fork and two branches, it should be understood that catheters of the present invention and systems/methods using them could include more than one fork and/or that each fork could include two or more branches.

One or more of the infusion sections on a branched catheter may preferably include a permeable membrane as described in connection with other embodiments herein. The permeable membranes used in the various infusion sections may have the same characteristics or they may be different. For example, the permeable membrane in each infusion section may have the same pore size if it is desired to have an equal amount of drug be infused from each infusion section. Sometimes, however, it may be desired to distribute different amounts of drug to two or more of the infusion sections. To do so, for example, the pore size of the permeable membranes in the different infusion sections could potentially be selected to provide the desired relative distribution. For example, a larger pore size could be expected to allow more drug to pass through the membrane, while a smaller pore size could be expected to allow less drug to pass through the membrane.

The branched catheter 920 could be designed with a single lumen that splits at fork 923 to service the infusion sections 927a and 927b on branch 920a and infusion section 927c on branch 920b. Alternatively, however, multiple lumens could be provided to service each of the infusion sections 927a,

927b, and 927c separately. Such a configuration could allow for the delivery of different drug solutions to the different infusion sections 927a, 927b, and 927c as discussed herein with respect to multiple lumen catheters that are not branched. In still another variation, one infusion section could be serviced by a first lumen and two or more infusion sections (on the same or different branches) could be served by a common lumen (that splits if the commonly-served infusion sections are located on different branches.

In various embodiments, the invention provides methods for treating disease, methods for optimizing therapy, methods for screening patients. In the context of the present invention, the terms "treat", "therapy", and the like are meant to include methods to alleviate, slow the progression, prevent, attenuate, or cure the treated disease. The systems and catheters described herein may be employed in the various methods.

In various embodiments, the invention provides a method for treating a disease associated with two or more spinal locations. The method comprises administering a first therapeutic composition to a first spinal location and administering a second therapeutic composition to a second location. As used herein, "therapeutic composition" means a composition comprising a drug as discussed herein. Therapeutic compositions may comprise one or more drug. Preferably therapeutic compositions are solutions. The method may further comprise administering a third therapeutic composition to a third spinal location. Fourth, fifth, sixth, etc. therapeutic compositions may be administered to fourth, fifth, sixth, etc. spinal locations. Each spinal location is at least one vertebral level from the other the spinal locations. Two or more of the first, second, third, etc. therapeutic compositions may include one or more of the same drugs, or each therapeutic composition may include different drugs. Two or more of the first, second, third, etc. therapeutic compositions may include substantially the same excipients, carriers, dilutents, etc. or each may include different excipients, carriers, dilutents, etc. An administered therapeutic composition refers to a therapeutic composition as delivered to a subject and may result from mixing of two or more therapeutic compositions prior to administration. In an embodiment, mixing may occur in a device. Mixing may occur as described herein with regard to a system as described in, e.g., FIG. 5. The first and second location (and third, fourth, fifth, etc. locations) may be the same if a first and second therapeutic compositions are different and the delivery of the first and second drug to the same location are independently controlled.

Delivery of a therapeutic to a spinal region may be accomplished through any medically acceptable route of administration. Non-limiting examples of acceptable roots of administration include intrathecal, epidural, intradiscal, into nerve routes, into ligaments or tendons between or surrounding vertebrae, subcutaneous, and intramuscular. Any suitable means for delivering a therapeutic composition to a spinal region may be used. For example, the therapeutic composition may be placed under the skin of a subject in proximity to the subjects spinal cord or canal, the therapeutic composition may be injected via a medically acceptable route from a syringe through a needle, the therapeutic composition may be infused through a catheter 20, and the like. A catheter 20 may be coupled to a syringe or a pump assembly 10. Delivery of each therapeutic composition to each spinal location may occur through the same or different routes. A single means or multiple means of delivery may be used to deliver each therapeutic composition to each spinal location.

When a single means is used to deliver multiple therapeutic agents to multiple spinal locations, the single means may be a catheter 20 having two or more infusion sites, as described herein. Such a catheter 20 may have a single lumen 26 or multiple lumens 26, as described herein. The catheter may be coupled to a pump assembly 10 having a single reservoir or multiple reservoirs. When a pump assembly 10 having a single reservoir is used, the multiple therapeutic compositions are the same. One or more infusion site may be covered by one or more permeable membranes 225.

The efficacy of a given therapy may be enhanced by modifying parameters including infusion rate, site of infusion, hydrophobicity, baricity, drug composition, tortuosity (lambda), viscosity, volume fraction (alpha), molecular weight, free diffusion coefficient, osmolarity, catheter design, or a combination thereof. Such parameters may be varied to alter efficacy when a drug is delivered through any route. For exemplary purposes, a discussion of modifying such parameters in the context of an intrathecally delivered therapy will be discussed. When a drug is delivered intrathecally, infusion rate may affect distribution of the drug and thus may affect efficacy. Although not wishing to be bound by theory, it is theorized that a decreasing infusion rate will result in more equitably radial distribution of a drug within the spinal canal. It is also theorized that increasing infusion rate will result in wider vertebral distribution of a drug in the spinal canal. Varying the concentration of a drug in a therapeutic composition may be desirable whether or not infusion rate is varied. Varying drug concentration coupled with varying infusion rate may allow for maintaining a substantially constant dosage or may allow for changing the dosage. Similarly, hydrophobicity of a drug or a solution carrying a drug may be varied to affect efficacy. A more hydrophobic drug or solution would be expected to have a more narrow axial distribution within the spinal canal than a more hydrophilic drug or solution. A drug for treatment of the particular disease may be substituted for another drug for treatment of the same disease. In some situations, a given drug may be more efficacious than another drug, or may provide fewer side effects. The site of administration of a drug may be varied to affect efficacy. This may be done by physically moving a catheter 20 such that an infusion site is located in a spinal region where drug action is desired. Alternatively, this can be accomplished by selecting an alternative infusion site of a catheter 20 that may be located at a more desirable location within the spinal canal. Similarly, the baricity of a solution containing a drug may be varied. The baricity may be increased if it is desired to target a drug to a location at a vertebral level lower than the location of an infusion site or a catheter 20. Alternatively, the baricity may be decreased if it is desired to target a drug to a location at a vertebral level higher than the location of an infusion site. A permeable membrane 225 may be added to one or more infusion site if more effective mixing with CSF is desired. Alternatively, an infusion site covered by a permeable membrane 225 or not covered by a permeable membrane 225 may be selected. The inter-relatedness of such parameters has not been completely discussed, but will be evident to one of ordinary skill in the art. While such parameters have been described in the context of treating a disease, it will be understood that such parameters may be varied in the context of screening patients to determine if therapy may be effective or trialing to determine appropriate parameters for therapy. It will be understood that the desired location of drug action may change over time and that the above parameters may be changed to enhance efficacy.

In an embodiment, the invention provides a method for treating pain. According to the International Association for the Study of Pain (IASP), "Pain is an unpleasant sensory and emotional experience associated with actual or potential tissue damage, or described in terms of such damage." When pain is no longer associated with actual or potential tissue damage, it is considered chronic pain. The method may be effective in treating pain, whether acute, chronic or both. For treatment of chronic pain, a system comprising an implantable therapeutic infusion pump assembly 10 is preferably used.

The method for treating pain comprises administering a first therapeutic composition to a first spinal location and a second therapeutic composition to a second spinal location. In part, such a method may be beneficial because nerve roots do not have a single junction with nerve cells in the spinal cord, but split into many branches in both directions. Thus treatment at several vertebral levels may be desirable. For example, patients with low back and/or leg pain may benefit from administration of a drug to the sacral nerve roots, which are typically in the area of S2 to L1, and administration of a drug to the lumbar enlargement, which is typically between L1 and T10. One of skill in the art will recognize other areas of the spinal column associated with pain in other regions of the body and can readily determine the appropriate spinal location for administration of a therapeutic composition. Further, it will be understood that patients suffering from pain in more than one location may also benefit from strategic administration of therapeutic compositions to more than one spinal location.

When used for treating pain, therapeutic compositions comprise one or more drugs in amounts effective to treat pain when administered through a chosen route. It will be recognized that the amount of the one or more drugs administered to a single spinal location may be ineffective for treating pain, but will be effective in combination with the one or more drugs administered to one or more additional spinal locations. Pain may be treated in any medically acceptable manner. Non-limiting examples of how pain may be treated include inhibiting signal transmission through nerve fibers, inhibiting signal transmission across a synapse in gray matter, enhancing descending inhibitors signals, and reducing inflammation. Any drug capable of treating pain in such a manner may be used. For example, signal transmission through nerve fibers may be inhibited by local anesthetics, such as bupivacaine, signal transmission across a synapse in gray matter may be inhibited by an opioid agonist, such as morphine, descending inhibitory signals may be enhanced by alpha-2 adrenergic agonists, such as clonidine, and inflammation may be reduced by steroids, such as prednisone, or non-steroidal anti-inflammatory agents (NSAIDS), such as ketorolac. For any given type of pain administration to more than one spinal location may be desirable. Non-limiting examples of types of pain include nociceptive pain, neuropathic pain and mixed pain (i.e., nociceptive and neuropathic pain).

Embodiments of a method for treating pain according to the invention include treating nociceptive pain. Nociceptive pain, which originates in the viscera or limbs, is caused by actual or potential tissue damage and is conveyed to the brain via afferent pain fibers through the dorsal horn of the spinal cord. Afferent pain fibers enter the spinal cord at different locations depending on the origin of nociceptive pain. Thus, it may be desirable to deliver a therapeutic composition to a spinal location associated with pain being sensed by a patient. Neuropathic pain can be caused by damage to the peripheral or central nervous system (nerve damage). Any antinociceptive drug may be used to treat nociceptive pain. Antinociceptive agents are known and include opioid agonists, non-steroidal anti-inflammatory drugs (NSAIDs), and GABA agonists such as baclofen. Exemplary opioid agonists include morphine and hydromorphone. Ranges of effective daily doses of such drugs are known by physicians. For example, morphine is typically administered intrathecally at a daily dose range of between 0.5 mg/day and 20 mg/day.

Embodiments of a method for treating pain according to the invention include treating neuropathic pain. Neuropathic pain as defined by IASP is: "pain initiated or caused by a primary lesion or dysfunction in the nervous system". Classic examples of neuropathic pain include: trigeminal neuralgia, complex regional pain syndrome (CRPS), post herpetic neuralgia, diabetic neuropathy, and pain associated with plexopathy and radiculopathy. The etiology of neuropathic pain is typically classified according to the insult/injury to the nervous system or the anatomical distribution of the pain. It is generally classified as peripheral nerve injury such as polyneuropathy (e.g. diabetes, HIV, alcohol) and mononeuropathy or multiple mononeuropathy (e.g. diabetes, cancer, postherpetic neuralgia, ischemic neuropathy) as well as central nervous system injury (e.g. post stroke pain, spinal injury, multiple sclerosis). Regardless of the etiology, a method according to the invention may be used to treat neuropathic pain. It will be understood that the location of intrathecal delivery of a therapeutic composition may be adjusted to an appropriate level of the spinal cord based on the origin of the neuropathy. Any antineuropathic pain drug may be used to treat neuropathic pain. Antineuropathic pain drugs are known and include local anesthetics, alpha2-adrenergic agonists and/or GABA agonists such as baclofen. Opioids and NSAIDS may be used, although neuropathic pain is considered less responsive to typical analgesics such as opioids and NSAIDs. Adjuvant analgesic agents, such as anticonvulsants and antidepressants may also be used for treating neuropathic pain. Ranges of effective daily doses of such drugs are known by physicians. For example, bupivicaine is typically administered intrathecally at a daily dose range of between 0.5 mg/day and 7.5 mg/day.

Embodiments of the method for treating pain according to the invention include treating mixed pain. "Mixed pain" refers to pain that emerges from both nociceptive and neuropathic sources. Any mixed pain may be treated according to the invention. Exemplary types of mixed pain that may be treated include chronic back and leg pain. Antinociceptive drugs, antineuropathic pain drugs, and combinations thereof may be used to treat mixed pain. In a particular embodiment, low back pain and/or leg pain is treated by administering bupivcaine to a spinal location occupied by the sacral nerve roots and administering morphine to a spinal location occupied by the lumbar enlargement.

It will be understood that parameters including infusion rate, site of infusion, hydrophobicity, baricity, drug composition, catheter design, or a combination thereof may be altered based upon the response of a patient to the therapeutic agent. Any measure of pain improvement or worsening may be used to evaluate whether a therapy modification may be appropriate. Such determinations can be readily made by, for example, a physician attending to the patient's care. In an embodiment, a Visual Analog Scale (VAS) is used to assess pain. The VAS is typically either a horizontal or vertical straight line; usually 10 cm in length with the descriptors of "least possible pain" or "no pain" on one end and "worst possible pain" on the other. The patient marks on the line where their pain level is at the present moment. The distance from the patient's mark to the end of the line is the measure of severity of the pain. The measurement is reproducible, as shown in the correlation coefficients between successive measurements. It is one of the most sensitive measurements of pain. The VAS is easy to administer and understand. It has been administered to children as young as 5 years of age and they were able to use the scale.

It will be understood that the amount of drug delivered or the location in which drug is delivered may be adjusted based upon the presentation and severity of side effects in a patient. Side effects may be recognizable by the patient, a physician attending to the care of the patient, other health care professionals, and the like. A physician or other health care professional may adjust therapy parameters based on side effects.

In an embodiment, the invention provides a method for treating spasticity. Spasticity is a result of increased muscle tone associated with an imbalance in motor pathways and associated feedback mechanisms. For a more detailed discussion of spasticity, see e.g. Vanek and Menkes, Spasticity, available at http://www.emedicine.com/neuro/topic706.htm. For a more detailed discussion of motor pathways and associated feedback mechanisms, see e.g. Kandel et al., Principles of Neuroscience, $3^{rd}$ ed., 1991, Appleton & Lange, East Norwalk, Conn. (Library of Congress Catalog Card No. 92-055057), particularly chapters 35-39. The method for treating spasticity comprises administering a first therapeutic composition to a first spinal location and a second therapeutic composition to a second spinal location. In an embodiment, the first spinal location is a location associated with control of lower limb spasticity (approximately T10-L1) and the second location is associated with control of upper limb spasticity (C1-C7). Delivery of a therapeutic composition to two separate spinal locations may provide greater efficacy and produce fewer and/or less severe side effects.

Generally any drug that can enhance or mimic inhibitory neural activity may be used to treat spasticity. Such drugs are known and include GABA agonists, such as baclofen, benzodiazapines such as diazepam and clonazepam, and alpha2 adrenergic agonists such as tizanidine. Opioid agonists such as morphine may also be efficacious in the treatment of spasticity, particularly when administered intrathecally. Ranges of effective daily doses of such drugs are known by physicians. For example, baclofen is typically administered intrathecally at a daily dose range of between 0.02 mg/day and 5 mg/day.

In a particular embodiment, a method for treating spasticity comprises administering baclofen intrathecally to a spinal location between T10 and L1 and to a spinal location between C1 and C7.

An embodiment of the invention provides a method for delivering a drug to a subject's brain via the subject's spinal canal. The method comprises administering a hypobaric solution comprising the drug to the subject's cerebrospinal fluid (CSF) in a spinal location. The drug may be infused through an infusion section of a catheter. The method may be advantageous because intrathecal delivery of a drug generally in considered less complicated and thus more safe than intraparenchymal delivery. The drug may enter the brain through CSF, as there is communication between CSF in the brain and in the spinal canal. Infusing a hybobaric drug into a subject's spinal CSF may facilitate delivery of the drug the brain. As people sit and stand upright, buoyant forces will carry the drug upward towards the brain. If drug is infused in a location high in the spinal canal (e.g., the cervical region), the drug may reach the brain within seconds or minutes, as opposed to infusion of isobaric drugs in the lumbar region, which may take hours for the drug to reach the brain. Not only can the drug reach the brain more quickly, a higher concentration of the drug can reach the brain as the longer the drug is in the spinal cord, the more likely that the drug will diffuse out of the CSF. In addition, the drug or solution carrying the drug may be made hydrophilic (more soluble in aqueous solutions, such as CSF, than in lipids, such as tissue surrounding the spinal canal). The more hydrophilic the drug, the more likely the drug will remain in the CSF for longer time. The longer the drug remains in the CSF, the more likely it will reach the brain. In an embodiment, the drug or solution carrying the drug is sufficiently hydrophilic that the drug may reach the brain in a concentration effective to treat a disease.

An embodiment of the invention provides a method for reducing the amount of a drug that reaches a subject's brain when introduced intrathecally. The method comprises infusing a hyperbaric drug into the subject's spine. The method may be advantageous because it may be desirable to keep certain drugs from reaching the brain, where the drug may act to produce side effects. To maximize the amount of drug kept out of the brain, the drug may be infused at a low spinal location, such as the lumbar region.

An embodiment of the invention provides a method for infusing a drug into the brain as described above and infusing a drug into the spine. It will be recognized that certain drugs may have additive or super-additive effects when administered to both the brain the spinal cord. Morphine for treating pain presents one such example.

The publications discussed herein are provided solely for their disclosure prior to the filing date of the present application. All publications mentioned herein are incorporated by reference to disclose and describe the methods and/or materials in connection with which the publications are cited. Nothing herein is to be construed as an admission that the present invention is not entitled to antedate such publication by virtue of prior invention. Further, the dates of publication provided may be different from the actual publication dates which may need to be independently confirmed.

All drugs referred to herein by a particular name should be construed to include salts, polymorphs, and hydrates thereof.

As used herein and in the appended claims, the singular forms "a," "and," and "the" include plural referents unless the context clearly dictates otherwise. Thus, for example, reference to "a drug" includes a plurality of drugs and reference to "the lumen" includes reference to one or more lumens and equivalents thereof known to those skilled in the art.

Unless otherwise indicated, all numbers expressing measurements, pore sizes, etc. used in the specification and claims are to be understood as preferably being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A drug delivery catheter comprising:
an elongated body comprising a proximal end and distal end;
a lumen extending along the elongated body to a first infusion section spaced from the proximal end of the elongated body;
one or more openings in the lumen within the first infusion section;
a permeable membrane covering the one or more openings in the first infusion section;
a first tracking element attached to the elongated body at a first selected location proximate the first infusion section to allow a practitioner to determine the position of the first infusion section, wherein the first tracking element comprises an active tracking element comprising a transmitter; and
a second tracking element, wherein the second tracking element is attached to the elongated body at a second selected location, and wherein the second tracking element operates on a different modality than the first tracking element.

2. The catheter of claim 1, wherein the second location is proximate the first infusion section.

3. The catheter of claim 1, wherein the first infusion section comprises an axial length of 20 mm or more.

4. The catheter of claim 1, wherein the first infusion section comprises an axial length of 320 mm or less.

5. The catheter of claim 1, further comprising a second infusion section on the elongated body.

6. The catheter of claim 5, wherein the second selected location is proximate the second infusion section.

7. The catheter of claim 5, wherein the first infusion section is spaced apart from the second infusion section along the elongated body by an axial distance of 20 mm or more.

8. The catheter of claim 5, wherein the first infusion section is spaced apart from the second infusion section along the elongated body by an axial distance of one human vertebral level or more.

9. The catheter of claim 1, further comprising a guidewire lumen extending from the proximal end of the elongated body to the distal end of the elongated body.

10. The catheter of claim 9, further comprising a guidewire located within the guidewire lumen.

11. The catheter of claim 10, wherein the guidewire comprises a steerable guidewire.

12. The catheter of claim 10, wherein the guidewire comprises a guidewire tracking element proximate a distal end of the guidewire.

13. A drug delivery system comprising:
a drug delivery apparatus comprising a pump and a drug reservoir;
a catheter comprising:
an elongated body comprising a proximal end and distal end;
a lumen extending along the elongated body to a first infusion section spaced from the proximal end of the elongated body;
one or more openings in the lumen within the first infusion section;
a permeable membrane covering the one or more openings in the first infusion section;
a first tracking element attached to the elongated body at a first selected location proximate the first infusion section to allow a practitioner to determine the position of the first infusion section, wherein the first tracking element comprises an active tracking element comprising a transmitter; and
a second tracking element, wherein the second tracking element is attached to the elongated body at a second selected location, and wherein the second tracking element operates on a different modality than the first tracking element; and
a tracking system adapted to determine the location of the first tracking element.

14. The system of claim 13, wherein the second location is proximate the first infusion section.

15. The system of claim 13, wherein the first infusion section comprises an axial length of 20 mm or more.

16. The system of claim 13, wherein the first infusion section comprises an axial length of 320 mm or less.

17. The system of claim 13, further comprising a second infusion section on the elongated body.

18. The system of claim 17, wherein the second selected location is proximate the second infusion section.

19. The system of claim 17, wherein the first infusion section is spaced apart from the second infusion section along the elongated body by an axial distance of 20 mm or more.

20. The system of claim 17, wherein the first infusion section is spaced apart from the second infusion section along the elongated body by an axial distance of one human vertebral level or more.

21. The system of claim 13, further comprising a guidewire lumen extending from the proximal end of the elongated body to the distal end of the elongated body.

22. The system of claim 21, further comprising a guidewire located within the guidewire lumen.

23. The system of claim 22, wherein the guidewire comprises a steerable guidewire.

24. The system of claim 22, wherein the guidewire comprises a guidewire tracking element proximate a distal end of the guidewire.

25. The system of claim 13, wherein the drug delivery apparatus comprises an implantable drug delivery apparatus.

26. A drug delivery catheter comprising:
an elongated body comprising a proximal end and distal end;
a lumen extending along the elongated body to a first infusion section spaced from the proximal end of the elongated body;
one or more openings in the lumen within the first infusion section;
a permeable membrane covering the one or more openings in the first infusion section;
a first tracking element attached to the elongated body at a first selected location proximate the first infusion section to allow a practitioner to determine the position of the first infusion section;
a second infusion section on the elongated body; and
a second tracking element, wherein the second tracking element is attached to the elongated body at a second selected location that is proximate the second infusion section, and wherein the second tracking element operates on a different modality than the first tracking element.

27. The catheter of claim 26, wherein the first tracking element comprises a passive tracking element.

28. The catheter of claim 26, wherein the second location is proximate the first infusion section.

29. The catheter of claim 26, wherein the first infusion section comprises an axial length of 20 mm or more.

30. The catheter of claim 26, wherein the first infusion section comprises an axial length of 320 mm or less.

31. The catheter of claim 26, wherein the first infusion section is spaced apart from the second infusion section along the elongated body by an axial distance of 20 mm or more.

32. The catheter of claim 26, wherein the first infusion section is spaced apart from the second infusion section along the elongated body by an axial distance of one human vertebral level or more.

33. The catheter of claim 26, further comprising a guidewire lumen extending from the proximal end of the elongated body to the distal end of the elongated body.

34. The catheter of claim 33, further comprising a guidewire located within the guidewire lumen.

35. The catheter of claim 34, wherein the guidewire comprise a steerable guide wire.

36. The catheter of claim 34, wherein the guide wire comprise a guidewire tracking element proximate a distal end of the guidewire.

37. A drug delivery system comprising:
   a drug delivery apparatus comprising a pump and a drug reservoir;
   a catheter comprising:
      an elongated body comprising a proximal end and distal end;
      a lumen extending along the elongated body to a first infusion section spaced from the proximal end of the elongated body;
      one or more openings in the lumen within the first infusion section;
      a permeable membrane covering the one or more openings in the first infusion section;
      a first tracking element attached to the elongated body at a first selected location proximate the first infusion section to allow a practitioner to determine the position of the first infusion section,
      a second infusion section on the elongated body;
      a second tracking element, wherein the second tracking element is attached to the elongated body at a second selected location that is proximate the second infusion section, and wherein the second tracking element operates on a different modality than the first tracking element; and
   a tracking system adapted to determine the location of the first tracking element.

38. The system of claim 37, wherein the first tracking element comprises a passive tracking element.

39. The system of claim 37, wherein the second location is proximate the first infusion section.

40. The system of claim 37, wherein the first infusion section comprises an axial length of 20 mm or more.

41. The system of claim 37, wherein the first infusion section comprises an axial length of 320 mm or less.

42. The system of claim 37, wherein the first infusion section is spaced apart from the second infusion section along the elongated body by an axial distance of 20 mm or more.

43. The system of claim 37, wherein the first infusion section is spaced apart from the second infusion section along the elongated body by an axial distance of one human vertebral level or more.

44. The system of claim 37, further comprising a guidewire lumen extending from the proximal end of the elongated body to the distal end of the elongated body.

45. The system of claim 44, further comprising a guidewire located within the guidewire lumen.

46. The system of claim 45, wherein the guidewire comprises a steerable guidewire.

47. The system of claim 45, wherein the guidewire comprises a guidewire tracking element proximate a distal end of the guidewire.

48. The system of claim 37, wherein the drug delivery apparatus comprises an implantable drug delivery apparatus.

* * * * *